(12) United States Patent
Ignatyev et al.

(10) Patent No.: US 8,916,729 B2
(45) Date of Patent: Dec. 23, 2014

(54) COMPOUNDS WITH (PERFLUOROALKYL) FLUOROHYDROGENPHOSPHATE ANIONS

(75) Inventors: Nikolai (Mykola) Ignatyev, Duisburg (DE); Michael Schulte, Bischofsheim (DE); Anne Julia Bader, Bielefeld (DE); Berthhold Theo Hoge, Bielefeld (DE)

(73) Assignee: Merck Patent GmbH, Darmstadt (DE)

( * ) Notice: Subject to any disclaimer, the term of this patent is extended or adjusted under 35 U.S.C. 154(b) by 336 days.

(21) Appl. No.: 13/516,029

(22) PCT Filed: Dec. 6, 2010

(86) PCT No.: PCT/EP2010/007397
§ 371 (c)(1), (2), (4) Date: Jun. 14, 2012

(87) PCT Pub. No.: WO2011/072810
PCT Pub. Date: Jun. 23, 2011

(65) Prior Publication Data
US 2012/0264946 A1 Oct. 18, 2012

(30) Foreign Application Priority Data
Dec. 18, 2009 (DE) .......................... 10 2009 058 969

(51) Int. Cl.
*C07F 9/535* (2006.01)
*C07F 9/30* (2006.01)
*C07F 9/38* (2006.01)
*C07F 9/48* (2006.01)
*C07F 9/54* (2006.01)

(52) U.S. Cl.
CPC ............... *C07F 9/535* (2013.01); *C07F 9/301* (2013.01); *C07F 9/3808* (2013.01); *C07F 9/4816* (2013.01); *C07F 9/5442* (2013.01)
USPC .......................................................... 568/16

(58) Field of Classification Search
CPC ..................................................... C07F 9/535
USPC .......................................................... 568/16
See application file for complete search history.

(56) References Cited

U.S. PATENT DOCUMENTS

| | | |
|---|---|---|
| 6,210,830 B1 | 4/2001 | Sartori et al. |
| 6,264,818 B1 | 7/2001 | Heider et al. |
| 6,841,301 B2 | 1/2005 | Heider et al. |
| 7,094,328 B2 | 8/2006 | Ignatyev et al. |
| 7,153,974 B2 | 12/2006 | Schmidt et al. |
| 7,208,626 B2 | 4/2007 | Welz-Biermann et al. |
| 7,632,969 B2 | 12/2009 | Welz-Biermann et al. |
| 2002/0015884 A1 | 2/2002 | Schmidt et al. |
| 2002/0022182 A1 | 2/2002 | Heider et al. |
| 2004/0171879 A1 | 9/2004 | Ignatyev et al. |
| 2005/0131256 A1 | 6/2005 | Welz-Biermann et al. |
| 2007/0191637 A1 | 8/2007 | Welz-Biermann et al. |

FOREIGN PATENT DOCUMENTS

| | | |
|---|---|---|
| DE | 196 41 138 A1 | 4/1998 |
| EP | 0 929 558 B1 | 1/2001 |
| EP | 1 162 204 A1 | 12/2001 |
| EP | 1 178 050 A2 | 2/2002 |
| WO | 98/15562 A1 | 4/1998 |
| WO | 00/21969 A1 | 4/2000 |
| WO | 02/085919 A1 | 10/2002 |
| WO | 03/002579 A1 | 1/2003 |
| WO | 03/087113 A1 | 10/2003 |

OTHER PUBLICATIONS

Wasserscheid, P. et al., "Ionische Flüssigkeiten—neue,, Lösungen" für die Übergangsmetallkatalyse, Angew. Chem., 2000, vol. 112, pp. 3926-3945, WILEY-VCH Verlag GmbH, Wienheim.
Ignat'ev, N., et al., "New ionic liquids with tris(perfluoroalkyl)trifluorophosphate(FAP) anions," Journal of Fluorine Chemistry, Jul. 18, 2005, vol. 126, pp. 1150-1159, Elsevier.
Ignat'ev, N., et al., "Electrochemical fluorination of trialkylphosphines," Journal of Fluorine Chemistry, 2000, vol. 103, pp. 57-61, Elsevier.
Semenii, V. et al., "Difluorotris(Perfluoralkyl) Phosphoranes," Institute of Organic Chemistry, Academy of Sciences of the Ukrainian SSR, Kiev, Translated from Zhurnal Obschei Khimii, vol. 55, No. 12, pp. 2716-2720, Dec. 1985, translation pp. 2415-2417, Plenum Publishing Corporation.
Nixon, J.F., et al., "Direct Oxidation of Phosphines by the Bifluoride Ion," Journal of the Chemical Society, Chemical Communications, Jan. 1, 1968, pp. 997-998, Chemical Society, Letchworth, GB.
Cavell, R.G. et al., "The Hydrotetrafluorotrifluoromethylphosphate Anion: CF3PF4H-," Proceedings of the Chemical Society, Jul. 1, 1964, p. 229, Chemical Society, London.
Nixon, J.F., et al., "Amine Substitution and Halogen Exchange Reactions of Dihalogenotrifluoromethylphosphines," Journal of the Chemical Society, Jan. 1, 1964, pp. 5983-5990, Chemical Society, Letchworth, GB.
Nixon, J.F., et al., "Phosphorus-Fluorine Compounds. Part XIX. Synthesis of, and Nuclear Magnetic Resonance Spectral Studies on, Hexaco-ordinate Fluorophosphate Anions containing Phosphorus-Hydrogen Bonds," Journals of the Chemical Society. A, Inorganic, Physical and Theoretical Chemistry, Jan. 1, 1970, pp. 2075-2080, Chemical Society, UK.
International Search Report, dated Apr. 8, 2011, issued in corresponding PCT/EP2010/007397.

*Primary Examiner* — Joseph Kosack
(74) *Attorney, Agent, or Firm* — Millen, White, Zelano & Branigan, P.C.

(57) ABSTRACT

The present invention relates to a process for the preparation of compounds with (perfluoroalkyl)fluorohydrogenphosphate anion, and to compounds containing (perfluoroalkyl) fluorohydrogenphosphate anion and to the use thereof.

27 Claims, No Drawings

COMPOUNDS WITH (PERFLUOROALKYL) FLUOROHYDROGENPHOSPHATE ANIONS

The present invention relates to a process for the preparation of compounds with (perfluoroalkyl)fluorohydrogenphosphate anion, and to compounds with (perfluoroalkyl)fluorohydrogenphosphate anion and to the use thereof.

Onium salts with perfluoroalkylfluorophosphate anions (FAP anions) are employed as ionic liquids and conductive salts [EP 0929558 B1, WO 02/085919 A1, EP 1162204 A1].

An ionic liquid is taken to mean salts which generally consist of an organic cation and an inorganic anion. They do not contain any neutral molecules and usually have melting points below 373 K [Wasserscheid P, Keim W, 2000, *Angew. Chem.* 112: 3926].

Onium salts with an organic cation and a perfluoroalkylfluorophosphate anion (FAP anion) are usually prepared via an exchange reaction of a water-soluble onium salt with, for example, a chloride, bromide, tetra-fluoroborate or triflate anion and perfluoroalkylfluorophosphoric acid (HFAP) or its alkali-metal salts in water [N. V. Ignatyev, U. Welz-Biermann, A. Kucheryna, G. Bissky, H. Willner, 2005, *J. Fluorine Chem.* 126: 1150-1159]. HFAP [WO 03/002579] and metal salts thereof can be prepared from tris(perfluoroalkyl)difluorophosphoranes, which can be obtained by electrochemical fluorination (Simons process) of trialkylphosphines [N. V. Ignatyev, P. Sartori, 2000, *J. Fluorine Chem.* 103: 57-61; WO 00/21969]. Organic salts with an FAP anion usually have limited water solubility and can easily be separated from by-products, which remain in the aqueous solution.

Ionic liquids with FAP anion have high electrochemical and thermal stability and low viscosity. Areas of application of these ionic liquids are found in organic chemistry (solvents, extraction media, etc.) and in the material sciences (heat-exchange media, lubricants, conductive salts, etc.). Ionic liquids having FAP anions are inert materials which have much better hydrolytic stability than, for example, ionic liquids having $PF_6^-$ anions. In some cases, however, a medium is desirable which can easily be broken down again after the respective process.

The aim of the present invention was thus firstly the provision of a novel process for the preparation of compounds containing (perfluoroalkyl)fluorohydrogenphosphate anions. A further aim of the present invention was the provision of novel compounds containing (perfluoroalkyl)fluorohydrogenphosphate anions.

WO 03/087113 discloses a process which facilitates the reduction of (perfluoroalkyl)fluorophosphoranes. Surprisingly, a process has now been found which facilitates the addition of a hydride ion onto the substrate during the reaction of (perfluoroalkyl)fluorophosphorane with a hydride ion donor, giving a (perfluoroalkyl)fluorohydrogenphosphate anion.

The present invention thus relates firstly to a process for the preparation of a compound of the formula (1)

$$[Kt]^{x+}[(C_nF_{2n+1})_zPF_{5-z}H]^-{}_x \qquad (1)$$

in which $[Kt]^{x+}$ is an inorganic or organic cation, where, in one step, a compound of the formula (2)

$$(C_nF_{2n+1})_zPF_{5-z} \qquad (2)$$

is reacted with a hydride ion donor,
and where, if $[Kt]^{x+}$ is an organic cation, a second step can optionally be carried out in which the product from the first step is reacted with a compound of the formula (3)

$$[Kt]^{x+}[X]^-{}_x \qquad (3),$$

in which $[Kt]^{x+}$ stands for an organic cation and $[X]^-$ stands for a hydrophilic anion,
in which n=1-8, x=1-4 and z=1-4.

In the literature, bis(trifluoromethyl)difluorohydrogenphosphate ($[(CF_3)_2PF_3H]^-$) and trifluoromethyltrifluorohydrogenphosphate ($[CF_3PF_4H]^-$) salts with $K^+$ cation and $[Me_2NH_2]^+$ cation are described [J. F. Nixon, J. R. Swain, 1968, *Chem. Comm.*: 997-998; J. F. Nixon, J. R. Swain, 1970, *J. Chem. Soc. A: Inorg. Phys. Theor.*: 2075-2080; R. G. Cavell, J. F. Nixon, 1964, *Proc. Chem. Soc.*: 229]. $K^+ [(CF_3)_2PF_3H]^-$ and $K^+ [CF_3PF_4H]^-$ salts are prepared in situ in a reaction of bis(trifluoromethyl)fluorophosphine ($(CF_3)_2PF$) or trifluoromethyldifluorophosphine ($CF_3PF_2$) with potassium bifluoride in a sealed test tube at 60 to 100° C. or in acetonitrile solution at room temperature. The corresponding salts with a $[Me_2NH_2]^+$ cation are obtained by the reaction of $CF_3PF_2$ or $(CF_3)_2PF$ with $Me_2NH$.

These salts have merely been investigated with the aid of $^{19}F$- and $^1H$-NMR spectroscopic measurements in the reaction mixture. For the synthesis of $[(CF_3)_2PF_3H]^-$ and $[CF_3PF_4H]^-$ salts by the method of J. F. Nixon and J. R. Swain, the two starting materials bis(trifluoromethyl)fluorophosphine $(CF_3)_2PF$ and trifluoromethyldifluorophosphine $CF_3PF_2$, which are in the gaseous state at room temperature and are highly air-sensitive, are necessary. These can be prepared in a complex, multistep synthesis process.

In accordance with the invention, hydride ion donors are compounds which are capable of releasing one or more hydride ions ($H^-$). In the process according to the invention, the hydride ion donor is preferably selected from the group comprising metal hydrides, borohydrides, hydridoborates and hydridoaluminates, but also tertiary and secondary amines.

In a particularly preferred embodiment, metal hydrides are employed; these are very particularly preferably $LiAlH_4$.

In a further particularly preferred embodiment, use is made of tertiary or secondary amines of the formula (11):

$$R^{14}{}_2N{-}CH_2R^{15} \qquad (11),$$

where
$R^{14}$ and $R^{15}$ on each occurrence, independently of one another, denotes
H, where a maximum of one substituent $R^{14}$ can be H,
straight-chain or branched alkyl having 1-20 C atoms,
straight-chain or branched alkenyl having 2-20 C atoms and one or more double bonds,
straight-chain or branched alkynyl having 2-20 C atoms and one or more triple bonds,
saturated, partially or fully unsaturated cycloalkyl having 3-7 C atoms, which may be substituted by alkyl groups having 1-6 C atoms,
where $R^{15}$ may also be Cl or F,
where $R^{15}$ may be fully substituted by fluorine and/or one or more $R^{14}$ and/or $R^{15}$ may be partially substituted by halogens or partially substituted by $-OR^{1*}$, $-NR^{1*}{}_2$, $-CN$, $-C(O)NR^{1*}{}_2$ or $-SO_2NR^{1*}{}_2$,
and where one or two non-adjacent carbon atoms which are not in the α-position of the radicals $R^{14}$ and/or $R_{15}$ may be replaced by atoms and/or atom groups selected from the group $-O-$, $-S-$, $-S(O)-$, $-SO_2-$, $-N^+R^{1*}{}_2-$, $-C(O)NR^{1*}-$, $-SO_2NR^{1*}-$ or $-P(O)R^{1*}-$;
in which $R^{1*}$ stands for non- or partially fluorinated $C_1$- to $C_6$-alkyl, $C_3$- to $C_7$-cycloalkyl, unsubstituted or substituted phenyl.

The hydride ion donor used after the process according to the invention can be employed either in excess or in equimolar amount, in each case based on the amount of (perfluoroalkyl)fluorophosphoranes employed. The hydride ion donor is preferably employed in equimolar amount.

(Perfluoroalkyl)fluorophosphoranes of the formula (2) can be prepared by conventional methods known to the person skilled in the art. These compounds are preferably prepared by electrochemical fluorination of suitable starting compounds [V. Y. Semenii et al., 1985, *Zh. Obshch. Khim.* 55 (12): 2716-2720; N. V. Ignatyev, P. Sartori, 2000, *J. Fluorine Chem.* 103: 57-61; WO 00/21969].

In the compound of the formula (2), z preferably stands for 2 or 3; this means that formula (2) is preferably selected from the group comprising $(C_nF_{2n+1})_3PF_2$ and $(C_nF_{2n+1})_2PF_3$. z is particularly preferably =3.

In the compounds of the formula (2), n likewise preferably stands for 2, 3 or 4, particularly preferably for 2 or 4. n very particularly preferably stands for 2, this means that a compound of the formula (2) is very particularly preferably $(C_2F_5)_zPF_{5-z}$.

The compounds of the formula (2) are thus very particularly preferably $(C_2F_5)_3PF_2$.

The cation $[Kt]^{x+}$ in formula (1) of the process according to the invention can be either an inorganic cation or an organic cation.

If an inorganic cation is present, this is preferably a metal cation. The metal cation is particularly preferably an alkali-metal cation, preferably a lithium, sodium or potassium cation.

If $[Kt]^{x+}$ in formula (1) is an organic cation, this is preferably selected, exactly like $[Kt]^{x+}$ in formula (3), from the group comprising ammonium, phosphonium, uronium, thiouronium, sulfonium, oxonium, guanidinium cations, heterocyclic cations and iminium cations, as defined below:

Ammonium cations are given by the general formula (4)

$$[NR_4]^+ \qquad (4),$$

where

R in each case, independently of one another, denotes

H, straight-chain or branched alkyl having 1-20 C atoms, straight-chain or branched alkenyl having 2-20 C atoms and one or more double bonds, straight-chain or branched alkynyl having 2-20 C atoms and one or more triple bonds, saturated, partially or fully unsaturated cycloalkyl having 3-7 C atoms, which may be substituted by alkyl groups having 1-6 C atoms, where one R may be fully substituted by fluorine and/or one or more R may be partially substituted by halogens, in particular —F and/or Cl, or partially substituted by —OR$^1$, —NR$^{1*}{}_2$, —CN, —C(O)NR$^1{}_2$ or —SO$_2$NR$^1{}_2$, and where one or two non-adjacent carbon atoms which are not in the α-position of the radical R may be replaced by atoms and/or atom groups selected from the group —O—, —S—, —S(O)—, —SO$_2$—, —N$^+$R$^1{}_2$—, —C(O)NR$^1$—, —SO$_2$NR$^1$— or —P(O)R$^1$—.

Phosphonium cations are given by the general formula (5)

$$[PR^2{}_4]^+ \qquad (5),$$

where

R$^2$ in each case, independently of one another, denotes

H where all substituents R$^2$ cannot simultaneously be H, NR$^1{}_2$, straight-chain or branched alkyl having 1-20 C atoms, straight-chain or branched alkenyl having 2-20 C atoms and one or more double bonds, straight-chain or branched alkynyl having 2-20 C atoms and one or more triple bonds, saturated, partially or fully unsaturated cycloalkyl having 3-7 C atoms, which may be substituted by alkyl groups having 1-6 C atoms, where one R$^2$ may be fully substituted by fluorine and/or one or more R$^2$ may be partially substituted by halogens, in particular —F and/or —Cl, or partially substituted by —OR$^1$, —CN, —C(O)NR$^1{}_2$ or —SO$_2$NR$^1{}_2$, and where one or two non-adjacent carbon atoms which are not in the α-position of the R$^2$, may be replaced by atoms and/or atom groups selected from the group —O—, —S—, —S(O)—, —SO$_2$—, —N$^+$R$^1{}_2$—, —C(O)NR$^1$—, —SO$_2$NR$^1$—, or —P(O)R$^1$—.

Cations of the formulae (4) and (5) in which all four or three substituents R and R$^2$ are fully substituted by halogens, for example the tris(trifluoromethyl)methylammonium cation, the tetra(trifluoromethyl)ammonium cation or the tetra (nonafluorobutyl)ammonium cation, are therefore excluded.

Uronium cations are given by the general formula (6)

$$[C(NR^3R^4)(OR^5)(NR^6R^7)]^+ \qquad (6)$$

and suitable thiouronium cations are given by the formula (7), $$[C(NR^3R^4)(SR^5)(NR^6R^7)]^+ \qquad (7),$$

where

R$^3$ to R$^7$ each, independently of one another, denote

H, NR$^{1*}{}_2$, straight-chain or branched alkyl having 1 to 20 C atoms, straight-chain or branched alkenyl having 2-20 C atoms and one or more double bonds, straight-chain or branched alkynyl having 2-20 C atoms and one or more triple bonds, saturated, partially or fully unsaturated cycloalkyl having 3-7 C atoms, which may be substituted by alkyl groups having 1-6 C atoms, where one or more of the substituents R$^3$ to R$^7$ may be partially substituted by halogens, in particular —F, or by —OH, —OR$^1$, —CN, —C(O)NR$^1{}_2$ or —SO$_2$NR$^1{}_2$, and where one or two non-adjacent carbon atoms which are not in the α-position of R$^3$ to R$^7$ may be replaced by atoms and/or atom groups selected from the group —O—, —S—, —S(O)—, —SO$_2$—, —N$^+$R$^1{}_2$—, —C(O)NR$^1$—, —SO$_2$NR$^1$—, or —P(O)R$^1$—.

Sulfonium cations are given by the general formula (12))

$$[(R^\circ)_3S]^+ \qquad (12),$$

where

R$^\circ$ stands for

NR'''$_2$, straight-chain or branched alkyl having 1-8 C atoms, saturated, partially or fully unsaturated cycloalkyl having 3-7 C atoms, which may be substituted by alkyl groups having 1-6 C atoms, where one or more of the substituents R$^\circ$ may be partially substituted by halogens, in particular —F, or by —OR''', —CN or —N(R''')$_2$.

Oxonium cations are given by the general formula (13)

$$[(R^{\circ*})_3O]^+ \qquad (13),$$

where

R$^{\circ*}$ stands for straight-chain or branched alkyl having 1-8 C atoms, saturated, partially or fully unsaturated cycloalkyl having 3-7 C atoms, which may be substituted by alkyl groups having 1-6 C atoms, where one or more of the substituents R$^{\circ*}$ may be partially substituted by halogens, in particular —F, or by —OR''', —CN or —N(R''')$_2$, in which R''' stands, independently of one another, for a straight-chain or branched $C_1$-$C_8$-alkyl.

R° and R°* here preferably stand for a straight-chain alkyl having 1-8 C atoms, unsubstituted phenyl, or phenyl which is substituted by $C_1$-$C_6$-alkyl, OR''', N(R''')$_2$, CN or F.

R''' preferably stands for a straight-chain alkyl having 1-8 C atoms, in particular methyl or ethyl.

Guanidinium cations are given by the general formula (8)

$$[C(NR^8R^9)(NR^{10}R^{11})(NR^{12}R^{13})]^+ \qquad (8),$$

where $R^8$ to $R^{13}$ each, independently of one another, denote H, $NR^{1*}_2$, straight-chain or branched alkyl having 1 to 20 C atoms, straight-chain or branched alkenyl having 2-20 C atoms and one or more double bonds, straight-chain or branched alkynyl having 2-20 C atoms and one or more triple bonds, saturated, partially or fully unsaturated cycloalkyl having 3-7 C atoms, which may be substituted by alkyl groups having 1-6 C atoms, where one or more of the substituents $R^8$ to $R^{13}$ may be partially substituted by halogens, in particular —F, or by —OR$^1$, —CN, —C(O)NR$^1_2$ or —SO$_2$NR$^1_2$, and where one or two non-adjacent carbon atoms which are not in the α-position of $R^8$ to $R^{13}$ may be replaced by atoms and/or atom groups selected from the group —O—, —S—, —S(O)—, —SO$_2$—, —N$^+$R$^1_2$—, —C(O)NR$^1$—, —SO$_2$NR$^1$—, or —P(O)R$^1$—.

Heterocyclic cations are given by the general formula (9)

$$[HetN]^+ \qquad (9),$$

where [HetN]$^+$ is a heterocyclic cation selected from the group comprising

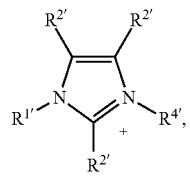
imidazolium

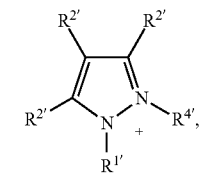
1H-pyrazolium

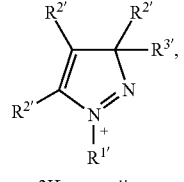
3H-pyrazolium

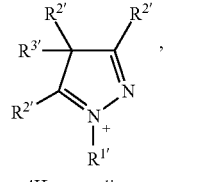
4H-pyrazolium

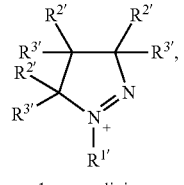
1-pyrazolinium

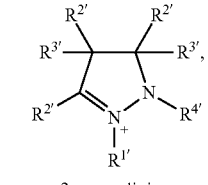
2-pyrazolinium

-continued

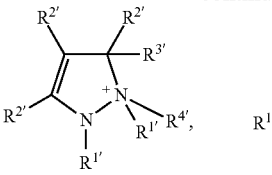
3-pyrazolinium

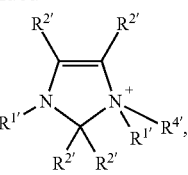
2,3-dihydroimidazolinium

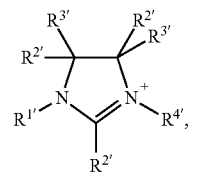
4,5-dihydroimidazolinium

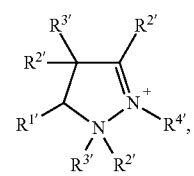
2,5-dihydroimidazolinium

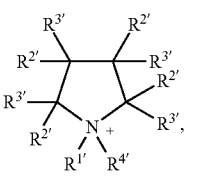
pyrrolidinium

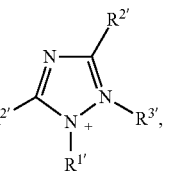
1,2,4-triazolium

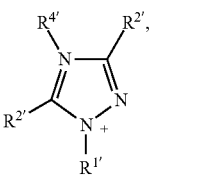
1,2,4-triazolium

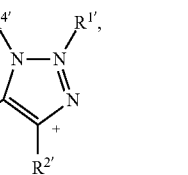
1,2,3-triazolium

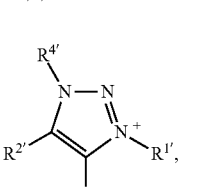
1,2,3-triazolium

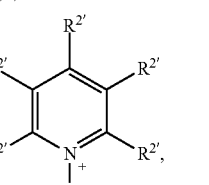
pyridinium

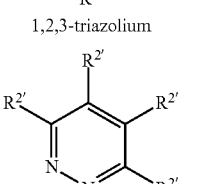
pyridazinium

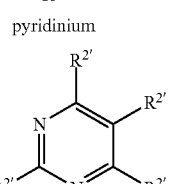
pyrimidinium

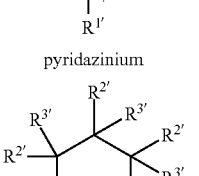
piperidinium

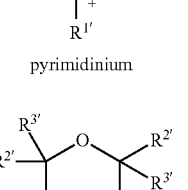
morpholinium

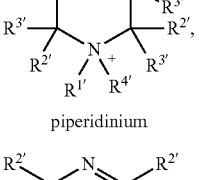
pyrazinium

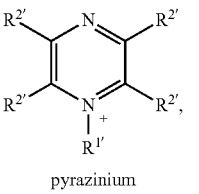
thiazolium

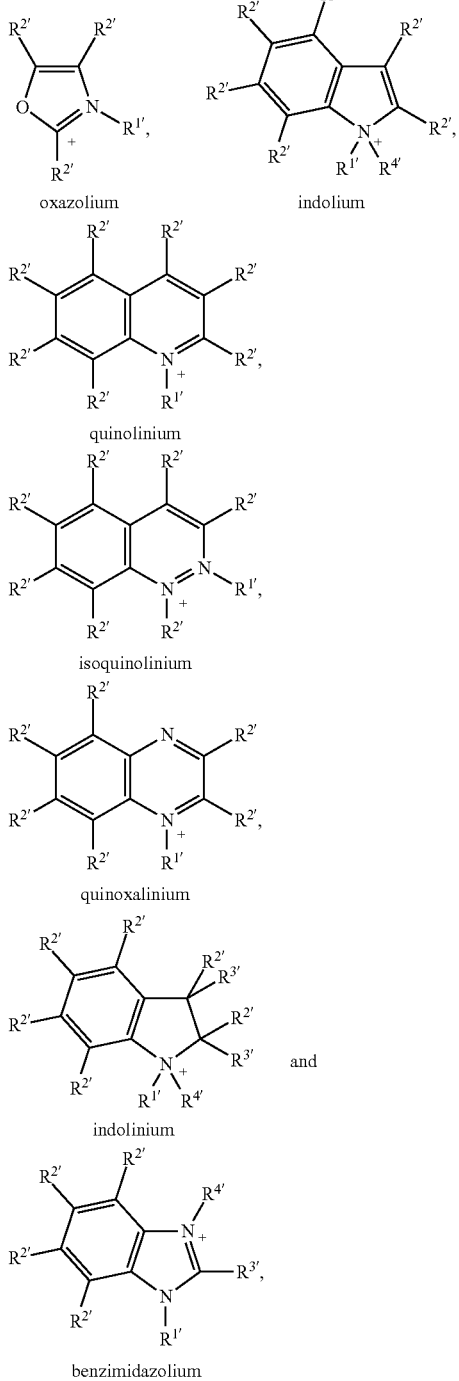

where the substituents $R^{1'}$ to $R^{4'}$ each, independently of one another, denote

H, straight-chain or branched alkyl having 1-20 C atoms, straight-chain or branched alkenyl having 2-20 C atoms and one or more double bonds, straight-chain or branched alkynyl having 2-20 C atoms and one or more triple bonds, saturated, partially or fully unsaturated cycloalkyl having 3-7 C atoms, which may be substituted by alkyl groups having 1-6 C atoms, saturated, partially or fully unsaturated heteroaryl, heteroaryl-$C_1$-$C_6$-alkyl or aryl-$C_1$-$C_6$-alkyl, where the substituents $R^{1'}$, $R^{2'}$, $R^{3'}$ and/or $R^{4'}$ together may form a ring system, where one or more substituents $R^{1'}$ to $R^{4'}$ may be partially or fully substituted by halogens, in particular —F and/or —Cl, or partially substituted by —$OR^1$, —CN, —$C(O)NR^1_2$ or —$SO_2NR^1_2$, but where $R^{1'}$ and $R^{4'}$ cannot simultaneously be fully substituted by halogens, and where one or two non-adjacent carbon atoms which are not bonded to the heteroatom of the substituents $R^{1'}$ to $R^{4'}$, may be replaced by atoms and/or atom groups selected from the group —O—, —S—, —S(O)—, —$SO_2$—, —$N^+R^1_2$—, —$C(O)NR^1$—, —$SO_2NR^1$—, or —$P(O)R^1$—.

Iminium cations are given by the general formula (10)

$$[R^{14}_2N=CHR^{15}]^+ \qquad (10),$$

where $R^{14}$ and $R^{15}$ on each occurrence, independently of one another, denotes H, where a maximum of one substituent $R^{14}$ can be H, straight-chain or branched alkyl having 1-20 C atoms, straight-chain or branched alkenyl having 2-20 C atoms and one or more double bonds, straight-chain or branched alkynyl having 2-20 C atoms and one or more triple bonds, saturated, partially or fully unsaturated cycloalkyl having 3-7 C atoms, which may be substituted by alkyl groups having 1-6 C atoms, where $R^{15}$ may also stand for Cl or F, where $R^{15}$ may be fully substituted by fluorine and/or one or more $R^{14}$ and/or $R^{15}$ may be partially substituted by halogens or partially substituted by —$OR^{1*}$, —$NR^{1*}_2$, —CN, —$C(O)NR^{1*}_2$ or —$SO_2NR^{1*}_2$, and where one or two non-adjacent carbon atoms which are not in the α-position of the radical $R^{14}$ and/or $R^{15}$ may be replaced by atoms and/or atom groups selected from the group —O—, —S—, —S(O)—, —$SO_2$—, —$N^+R^{1*}_2$—, —$C(O)NR^{1*}$—, —$SO_2NR^{1*}$— or —$P(O)R^{1*}$—;

$R^1$ in all above-mentioned definitions stands for H, non- or partially fluorinated $C_1$- to $C_6$-alkyl, $C_3$- to $C_7$-cycloalkyl, unsubstituted or substituted phenyl, and $R^{1*}$ stands for non- or partially fluorinated $C_1$- to $C_6$-alkyl, $C_3$- to $C_7$-cycloalkyl, unsubstituted or substituted phenyl.

Fully unsaturated cycloalkyl substituents in the sense of the present invention are also taken to mean aromatic substituents.

In accordance with the invention, suitable substituents R and $R^2$ to $R^{13}$ of the compounds of the formulae (4) to (8), besides H, are preferably: $C_1$- to $C_{20}$—, in particular $C_1$- to $C_{14}$-alkyl groups, and saturated or unsaturated, i.e. also phenyl, $C_3$- to $C_7$-cycloalkyl groups, which may be substituted by $C_1$- to $C_6$-alkyl groups, in particular phenyl.

The substituents R and $R^2$ in the compounds of the formula (4) or (5) may be identical or different. In compounds of the formulae (4), three or four substituents R are preferably identical. In compounds of the formulae (5), the substituents $R^2$ are preferably different.

The substituents R and $R^2$ are particularly preferably methyl, ethyl, isopropyl, propyl, butyl, sec-butyl, pentyl, hexyl, octyl, decyl or tetradecyl.

Up to four substituents of the guanidinium cation
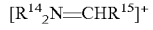 may also be connected in pairs in such a way that mono-, bi- or polycyclic molecules form.

Without restricting generality, examples of such guanidinium cations are:

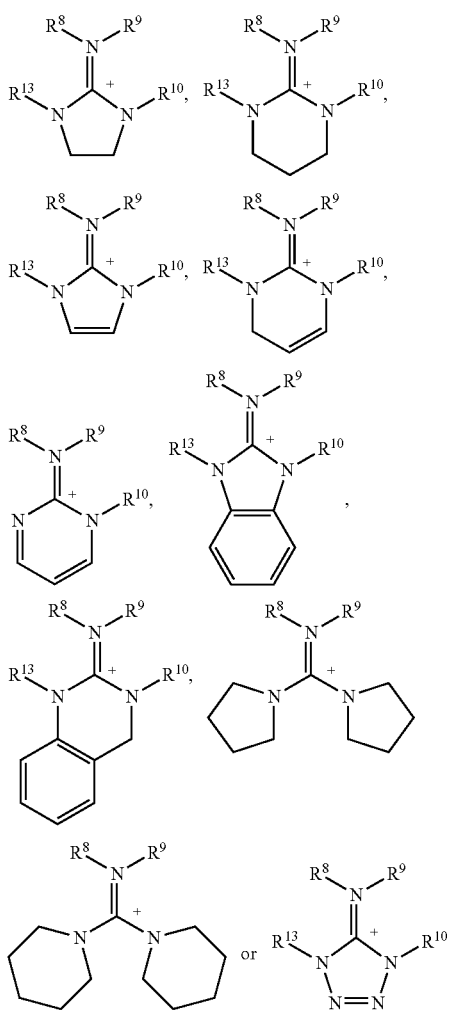

where the substituents $R^8$ to $R^{10}$ and $R^{13}$ may have an above-mentioned or particularly preferred meaning.

The carbocycles or heterocycles of the above-mentioned guanidinium cations may optionally also be substituted by $C_1$- to $C_6$-alkyl, $C_1$- to $C_6$-alkenyl, CN, $NR^1_2$, F, Cl, Br, I, $C_1$-$C_6$-alkoxy, $SCF_3$, $SO_2CF_3$ or $SO_2NR^1_2$, where $R^1$ has an above-mentioned meaning, substituted or unsubstituted phenyl or unsubstituted or substituted heterocycle.

Up to four substituents of the thiouronium cation $[C(NR^3R^4)(SR^5)(NR^6R^7)]^+$ may also be connected in pairs in such a way that mono-, bi- or polycyclic molecules form.

Without restricting generality, examples of such thiouronium cations are indicated below:

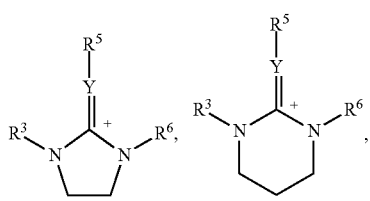

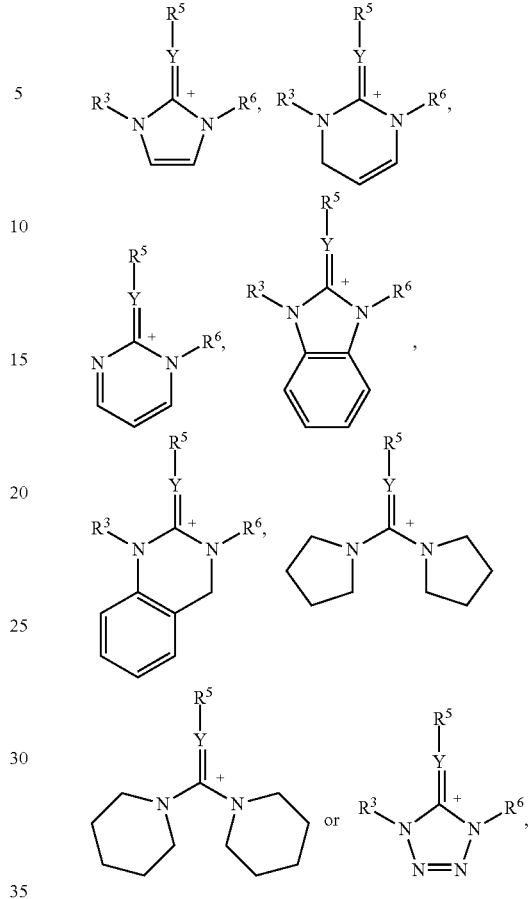

in which Y=S
and where the substituents $R^3$, $R^5$ and $R^6$ may have an above-mentioned or particularly preferred meaning.

The carbocycles or heterocycles of the above-mentioned molecules may optionally also be substituted by $C_1$- to $C_6$-alkyl, $C_1$- to $C_6$-alkenyl, CN, $NR^1_2$, F, Cl, Br, I, $C_1$-$C_6$-alkoxy, $SCF_3$, $SO_2CF_3$ or $SO_2NR^1_2$ or substituted or unsubstituted phenyl or unsubstituted or substituted heterocycle, where $R^1$ has an above-mentioned meaning.

The substituents $R^3$ to $R^{13}$ are each, independently of one another, preferably a straight-chain or branched alkyl group having 1 to 10 C atoms. The substituents $R^3$ and $R^4$, $R^6$ and $R^7$, $R^8$ and $R^9$, $R^{10}$ and $R^{11}$ and $R^{12}$ and $R^{13}$ in compounds of the formulae (7) and (8) may be identical or different. $R^3$ to $R^{13}$ are particularly preferably each, independently of one another, methyl, ethyl, n-propyl, isopropyl, n-butyl, tert-butyl, sec-butyl, phenyl or cyclohexyl, very particularly preferably methyl, ethyl, n-propyl, isopropyl or n-butyl.

In accordance with the invention, suitable substituents $R^{1'}$ to $R^{4'}$ of compounds of the formula (9), besides H, are preferably: $C_1$- to $C_{20}$, in particular $C_1$- to $C_{12}$-alkyl groups, and saturated or unsaturated, i.e. also aromatic, $C_3$- to $C_7$-cycloalkyl groups, which may be substituted by $C_1$- to $C_6$-alkyl groups, in particular phenyl.

The substituents $R^{1'}$ and $R^{4'}$ are each, independently of one another, particularly preferably methyl, ethyl, isopropyl, propyl, butyl, sec-butyl, pentyl, hexyl, octyl, decyl, cyclohexyl, phenyl or benzyl. They are very particularly preferably methyl, ethyl, n-butyl or hexyl. In pyrrolidine, piperidine, indoline, pyrrolidinium, piperidinium or indolinium compounds, the two substituents $R^{1'}$ and $R^{4'}$ are preferably different.

The substituent $R^{2'}$ or $R^{3'}$ is in each case, independently of one another, in particular H, methyl, ethyl, isopropyl, propyl, butyl, sec-butyl, tert-butyl, cyclohexyl, phenyl or benzyl. $R^{2'}$ is particularly preferably H, methyl, ethyl, isopropyl, propyl, butyl or sec-butyl. $R^{2'}$ and $R^{3'}$ are very particularly preferably H.

The $C_1$-$C_{12}$-alkyl group is, for example, methyl, ethyl, isopropyl, propyl, butyl, sec-butyl or tert-butyl, furthermore also pentyl, 1-, 2- or 3-methylbutyl, 1,1-, 1,2- or 2,2-dimethylpropyl, 1-ethylpropyl, hexyl, heptyl, octyl, nonyl, decyl, undecyl or dodecyl. Optionally difluoromethyl, trifluoromethyl, pentafluoroethyl, heptafluoropropyl or nonafluorobutyl.

In accordance with the invention suitable substituents $R^{14}$ and $R^{15}$ of the compounds of the formulae (10) and (11), besides H, are preferably: $C_1$- to $C_{20}$—, particularly preferably $C_1$- to $C_{14}$-alkyl groups and very particularly preferably $C_1$- to $C_4$-alkyl groups, which may in each case be unbranched or branched and where one or more radicals $R^{14}$ may be substituted by —$NR^{1*}_2$.

The substituents —$R^{14}$ and —$CH_2$—$R^{15}$ here may be identical or different. In a preferred embodiment, all three substituents —$R^{14}$ and —$CH_2$—$R^{15}$ are identical. In a further preferred embodiment, two of the substituents —$R^{14}$ and —$CH_2$—$R^{15}$ are identical.

The substituents $R^{14}$ are particularly preferably H, methyl, ethyl, isopropyl or dimethylaminomethyl.

The substituents $R^{15}$ are particularly preferably H or methyl.

The compound of the formula (11) is preferably selected from the compounds of the formula $N(CH_3)_3$, $N(C_2H_5)_3$, $HN(C_2H_5)_2$, $(CH_3)_2N$—$CH_2$—$N(CH_3)_2$ or $CH_3N((CH(CH_3)_2)_2$.

A straight-chain or branched alkenyl having 2 to 20 C atoms, where, in addition, a plurality of double bonds may be present, is, for example, allyl, 2- or 3-butenyl, isobutenyl, sec-butenyl, furthermore 4-pentenyl, isopentenyl, hexenyl, heptenyl, octenyl, —$C_9H_{17}$, —$C_{10}H_{19}$ to —$C_{20}H_{39}$; preferably allyl, 2- or 3-butenyl, isobutenyl, sec-butenyl, preference is furthermore given to 4-pentenyl, isopentenyl or hexenyl.

A straight-chain or branched alkynyl having 2 to 20 C atoms, where, in addition, a plurality of triple bonds may be present, is, for example, ethynyl, 1- or 2-propynyl, 2- or 3-butynyl, furthermore 4-pentynyl, 3-pentynyl, hexynyl, heptynyl, octynyl, —$C_9H_{15}$, —$C_{10}H_{17}$ to —$C_{20}H_{37}$, preferably ethynyl, 1- or 2-propynyl, 2- or 3-butynyl, 4-pentynyl, 3-pentynyl or hexynyl.

Aryl-$C_1$-$C_6$-alkyl denotes, for example, benzyl, phenylethyl, phenylpropyl, phenylbutyl, phenylpentyl or phenylhexyl, where both the phenyl ring and also the alkylene chain may be partially or fully substituted, as described above, by halogens, in particular —F and/or —Cl, or partially substituted by —$OR^1$, —$NR^1_2$, —CN, —$C(O)NR^1_2$, —$SO_2NR^1_2$.

Unsubstituted saturated or partially or fully unsaturated cycloalkyl groups having 3-7 C atoms are therefore cyclopropyl, cyclobutyl, cyclopentyl, cyclohexyl, cycloheptyl, cyclopentenyl, cyclohexenyl, phenyl, cycloheptenyl, each of which may be substituted by $C_1$- to $C_6$-alkyl groups, where the cycloalkyl group or the cycloalkyl group which is substituted by $C_1$- to $C_6$-alkyl groups may in turn also be substituted by halogen atoms, such as F, Cl, Br or I, in particular F or Cl, or by —$OR^1$, —CN, —$C(O)NR^1_2$, —$SO_2NR^1_2$.

In the substituents R, $R^2$ to $R^{13}$ or $R^{1'}$ to $R^{4'}$, one or two non-adjacent carbon atoms which are not bonded in the α-position to the heteroatom may also be replaced by atoms and/or atom groups selected from the group —O—, —S—, —S(O)—, —$SO_2$—, —$N^+R^1_2$—, —$C(O)NR^1$—, —$SO_2NR^1$—, or —$P(O)R^1$—, where $R^1$=non-, partially or perfluorinated $C_1$- to $C_6$-alkyl, $C_3$- to $C_7$-cycloalkyl, unsubstituted or substituted phenyl.

Without restricting generality, examples of substituents R, $R^2$ to $R^{13}$ and $R^{1'}$ to $R^{4'}$ modified in this way are: —$OCH_3$, —$OCH(CH_3)_2$, —$CH_2OCH_3$, —$CH_2$—$CH_2$—O—$CH_3$, —$C_2H_4OCH(CH_3)_2$, —$C_2H_4SC_2H_5$, —$C_2H_4SCH(CH_3)_2$, —$S(O)CH_3$, —$SO_2CH_3$, —$SO_2C_6H_5$, —$SO_2C_3H_7$, —$SO_2CH(CH_3)_2$, —$SO_2CH_2CF_3$, —$CH_2SO_2CH_3$, —O—$C_4H_8$—)—$C_4H_9$, —$CF_3$, —$C_2F_5$, —$C_3F_7$, —$C_4F_9$, —$C(CF_3)_3$, —$CF_2SO_2CF_3$, —$C_2F_4N(C_2F_5)C_2F_5$, —$CHF_2$, —$CH_2CF_3$, —$C_2F_2H_3$, —$C_3FH_6$, —$CH_2C_3F_7$, —$C(CFH_2)_3$, —$CH_2C_6H_5$ or $P(O)(C_2H_5)_2$.

In $R^1$, $C_3$- to $C_7$-cycloalkyl is, for example, cyclopropyl, cyclobutyl, cyclopentyl, cyclohexyl or cycloheptyl.

In $R^1$, substituted phenyl means phenyl which is substituted by $C_1$- to $C_6$-alkyl, $C_1$- to $C_6$-alkenyl, CN, $NR^1_2$, F, Cl, Br, I, $C_1$-$C_6$-alkoxy, $SCF_3$, $SO_2CF_3$ or $SO_2NR^*_2$, where R* denotes a non-, partially or perfluorinated $C_1$- to $C_6$-alkyl or $C_3$- to $C_7$-cycloalkyl, as defined for $R^1$, for example, o-, m- or p-methylphenyl, o-, m- or p-ethylphenyl, o-, m- or p-propylphenyl, o-, m- or p-isopropylphenyl, o-, m- or p-tert-butylphenyl, o-, m- or p-methoxyphenyl, o-, m- or p-ethoxyphenyl, o-, m-, p-(trifluoromethyl)phenyl, o-, m-, p-(trifluoromethoxy)phenyl, o-, m-, p-(trifluoromethylsulfonyl)phenyl, o-, m- or p-fluorophenyl, o-, m- or p-chlorophenyl, o-, m- or p-bromophenyl, o-, m- or p-iodophenyl, further preferably 2,3-, 2,4-, 2,5-, 2,6-, 3,4- or 3,5-dimethylphenyl, 2,3-, 2,4-, 2,5-, 2,6-, 3,4- or 3,5-dihydroxyphenyl, 2,3-, 2,4-, 2,5-, 2,6-, 3,4- or 3,5-difluorophenyl, 2,3-, 2,4-, 2,5-, 2,6-, 3,4- or 3,5-dichloro-phenyl, 2,3-, 2,4-, 2,5-, 2,6-, 3,4- or 3,5-dibromophenyl, 2,3-, 2,4-, 2,5-, 2,6-, 3,4- or 3,5-dimethoxyphenyl, 5-fluoro-2-methylphenyl, 3,4,5-trimethoxyphenyl or 2,4,5-trimethylphenyl.

In $R^{1'}$ to $R^{4'}$, heteroaryl is taken to mean a saturated or unsaturated mono- or bicyclic heterocyclic radical having 5 to 13 ring members, where 1, 2 or 3 N and/or 1 or 2 S or O atoms may be present and the heterocyclic radical may be mono- or polysubstituted by $C_1$- to $C_6$-alkyl, $C_1$- to $C_6$-alkenyl, CN, $NR^1_2$, F, Cl, Br, I, $C_1$-$C_6$-alkoxy, $SCF_3$, $SO_2CF_3$ or $SO_2NR^1_2$, where $R^1$ has a meaning indicated above.

The heterocyclic radical is preferably substituted or unsubstituted 2- or 3-furyl, 2- or 3-thienyl, 1-, 2- or 3-pyrrolyl, 1-, 2-, 4- or 5-imidazolyl, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -4- or -5-yl, 1- or 5-tetrazolyl, 1,2,3-oxadiazol-4- or -5-yl 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 2-, 3-, 4-, 5- or 6-2H-thiopyranyl, 2-, 3- or 4-4H-thiopyranyl, 3- or 4-pyridazinyl, pyrazinyl, 2-, 3-, 4-, 5-, 6- or 7-benzofuryl, 2-, 3-, 4-, 5-, 6- or 7-benzothienyl, 1-, 2-, 3-, 4-, 5-, 6- or 7-1H-indolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 1-, 2-, 3-, 4-, 5-, 6-, 7- or 8-quinolinyl, 1-, 3-, 4-, 5-, 6-, 7- or 8-isoquinolinyl, 1-, 2-, 3-, 4- or 9-carbazolyl, 1-, 2-, 3-, 4-, 5-, 6-, 7-, 8- or 9-acridinyl, 3-, 4-, 5-, 6-, 7- or 8-cinnolinyl, 2-, 4-, 5-, 6-, 7- or 8-quinazolinyl or 1-, 2- or 3-pyrrolidinyl.

Heteroaryl-$C_1$-$C_6$-alkyl is, analogously to aryl-$C_1$-$C_6$-alkyl, now taken to mean, for example, pyridinylmethyl, pyridinylethyl, pyridinylpropyl, pyridinylbutyl, pyridinylpentyl, pyridinylhexyl, where, furthermore, the heterocycles described above may be linked to the alkylene chain in this way.

HetN⁺ is preferably

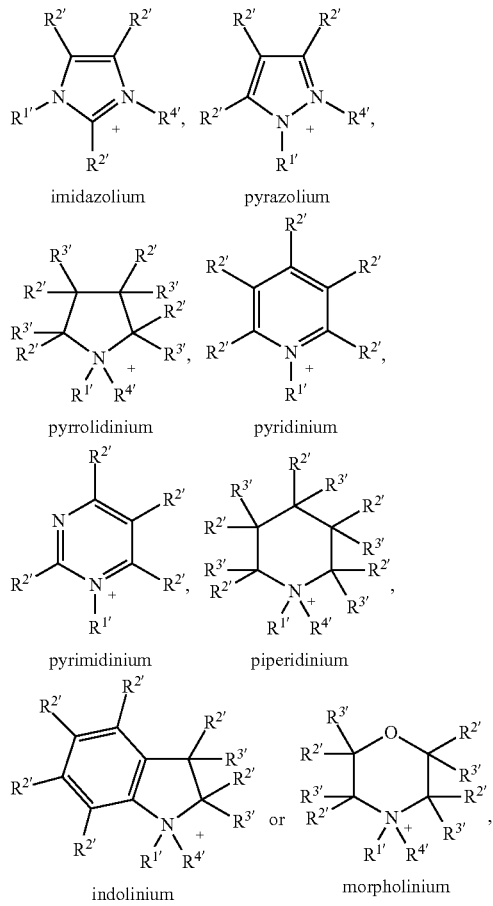

where the substituents $R^{1'}$ to $R^{4'}$ each, independently of one another, have a meaning described above.

The organic cation $[Kt]^{x+}$ is particularly preferably selected from the group comprising imidazolium, pyridinium, pyrrolidinium, ammonium, phosphonium or iminium cations, as defined above.

Particularly suitable imidazolium, pyrrolidinium and ammonium cations are selected from the group tetraalkylammonium, 1,1-dialkylpyrrolidinium, 1-alkyl-1-alkoxyalkylpyrrolidnium or 1,3-dialkylimidazolium, where the alkyl groups or the alkoxy group in the alkoxyalkyl group may each, independently of one another, have 1 to 10 C atoms. Very particularly preferably, the alkly groups have 1 to 6 C atoms and the alkoxy group has 1 to 3 C atoms. The alkyl groups in tetraalkylammonium can therefore be identical or different. Preferably, three alkyl groups are identical and one alkyl group is different or two alkyl groups are identical and the other two are different. Preferred tetraalkylammonium cations are, for example, trimethyl(ethyl)ammonium, triethyl(methyl)ammonium, tripropyl(methyl)ammonium, tributyl(methyl)ammonium, tripentyl(methyl)ammonium, trihexyl(methyl)ammonium, triheptyl(methyl)ammonium, trioctyl(methyl)ammonium, trinonyl(methyl)ammonium, tridecyl(methyl)ammonium, trihexyl(ethyl)ammonium, ethyl(trioctyl)ammonium, propyl(dimethyl)ethylammonium, butyl(dimethyl)-ethylammonium, methoxyethyl(dimethyl)ethylammonium, methoxyethyl(diethyl)methylammonium, methoxyethyl(dimethyl)propylammonium, ethoxyethyl(dimethyl)ethylammonium. Particularly preferred quaternary ammonium cations are propyl(dimethyl)ethylammonium and/or methoxyethyl(dimethyl)ethylammonium.

Preferred 1,1-dialkylpyrrolidinium cations are, for example, 1,1-dimethylpyrrolidinium, 1-methyl-1-ethylpyrrolidinium, 1-methyl-1-propylpyrrolidinium, 1-methyl-1-butylpyrrolidinium, 1-methyl-1-pentylpyrrolidinium, 1-methyl-1-hexylpyrrolidinium, 1-methyl-1-heptylpyrrolidinium, 1-methyl-1-octylpyrrolidinium, 1-methyl-1-nonylpyrrolidinium, 1-methyl-1-decylpyrrolidinium, 1,1-diethylpyrrolidinium, 1-ethyl-1-propylpyrrolidinium, 1-ethyl-1-butylpyrrolidinium, 1-ethyl-1-pentylpyrrolidinium, 1-ethyl-1-hexylpyrrolidinium, 1-ethyl-1-heptylpyrrolidinium, 1-ethyl-1-octylpyrrolidinium, 1-ethyl-1-nonylpyrrolidinium, 1-ethyl-1-decylpyrrolidinium, 1,1-dipropylpyrrolidinium, 1-propyl-1-methylpyrrolidinium, 1-propyl-1-butylpyrrolidinium, 1-propyl-1-pentylpyrrolidinium, 1-propyl-1-hexylpyrrolidinium, 1-propyl-1-heptylpyrrolidinium, 1-propyl-1-octylpyrrolidinium, 1-propyl-1-nonylpyrrolidinium, 1-propyl-1-decylpyrrolidinium, 1,1-dibutylpyrrolidinium, 1-butyl-1-methylpyrrolidinium, 1-butyl-1-pentylpyrrolidinium, 1-butyl-1-hexylpyrrolidinium, 1-butyl-1-heptylpyrrolidinium, 1-butyl-1-octylpyrrolidinium, 1-butyl-1-nonylpyrrolidinium, 1-butyl-1-decylpyrrolidinium, 1,1-dipentylpyrrolidinium, 1-pentyl-1-hexylpyrrolidinium, 1-pentyl-1-heptylpyrrolidinium, 1-pentyl-1-octylpyrrolidinium, 1-pentyl-1-nonylpyrrolidinium, 1-pentyl-1-decylpyrrolidinium, 1,1-dihexylpyrrolidinium, 1-hexyl-1-heptylpyrrolidinium, 1-hexyl-1-octylpyrrolidinium, 1-hexyl-1-nonylpyrrolidinium, 1-hexyl-1-decylpyrrolidinium, 1,1-dihexylpyrrolidinium, 1-hexyl-1-heptylpyrrolidinium, 1-hexyl-1-octylpyrrolidinium, 1-hexyl-1-nonylpyrrolidinium, 1-hexyl-1-decylpyrrolidinium, 1,1-diheptylpyrrolidinium, 1-heptyl-1-octylpyrrolidinium, 1-heptyl-1-nonylpyrrolidinium, 1-heptyl-1-decylpyrrolidinium, 1,1-dioctylpyrrolidinium, 1-octyl-1-nonylpyrrolidinium, 1-octyl-1-decylpyrrolidinium, 1-1-dinonylpyrrolidinium, 1-nony-1-decylpyrrolidinium or 1,1-didecylpyrrolidinium. Very particular preference is given to 1-butyl-1-methylpyrrolidinium or 1-propyl-1-methylpyrrolidinium.

Preferred 1-alkyl-1-alkoxyalkylpyrrolidinium cations are, for example, 1-methoxyethyl-1-methylpyrrolidinium, 1-methoxyethyl-1-ethylpyrrolidinium, 1-methoxyethyl-1-propylpyrrolidinium, 1-methoxyethyl-1-butylpyrrolidinium, 1-ethoxyethyl-1-methylpyrrolidinium, 1-ethoxymethyl-1-methylpyrrolidinium. Very particular preference is given to 1-methoxyethyl-1-methylpyrrolidinium.

Preferred 1,3-dialkylimidazolium cations are, for example, 1-ethyl-3-methylimidazolium, 1-methyl-3-propylimidazolium, 1-butyl-3-methylimidazolium, 1-methyl-3-pentylimidazolium, 1-ethyl-3-propylimidazolium, 1-butyl-3-ethylimidazolium, 1-ethyl-3-pentylimidazolium, 1-butyl-3-propylimidazolium, 1,3-dimethylimidazolium, 1,3-diethylimidazolium, 1,3-dipropypylimidazolium, 1,3-dibutylimidazolium, 1,3-dipentylimidazolium, 1,3-dihexylimidazolium, 1,3-diheptylimidazolium, 1,3-dioctylimidazolium, 1,3-dinonylimidazolium, 1,3-didecylimidazolium, 1-hexyl-3-methylimidazolium, 1-heptyl-3-methylimidazolium, 1-methyl-3-octylimidazolium, 1-methyl-3-nonylimidazolium, 1-decyl-3-methylimidazolium, 1-ethyl-3-hexylimidazolium, 1-ethyl-3-heptylimidazolium, 1-ethyl-3-octylimidazolium, 1-ethyl-3-nonylimidazolium or 1-decyl-3-ethylimidazolium.

Particularly preferred cations are 1-ethyl-3-methylimidazolium, 1-butyl-3-methylimidazolium or 1-methyl-3-propylimidazolium.

The organic cation [Kt]$^{x+}$ is very particularly preferably a cation selected from the group comprising 1-ethyl-3-methylimidazolium and 1-butyl-3-methylimidazolium.

In formula (3) of the process according to the invention, [X]$^-$ stands for a hydrophilic anion. This is preferably an anion selected from the group comprising Cl$^-$, Br$^-$, I$^-$, sulfate, sulfonate, acetate and BF$_4^-$.

A further very particularly preferred embodiment of the present invention is a process for the preparation of a compound of the formula (1) as defined above in which [Kt]$^{x+}$ is an iminium cation, where a compound of the formula (2) as defined above is reacted with a tertiary or secondary amine of the formula (11) as defined above. This embodiment has the advantage that a compound of the formula (1) containing the organic iminium cation can be prepared directly in one step without a subsequent metathesis reaction being necessary in a second step. The following reaction scheme illustrates this reaction by way of example:

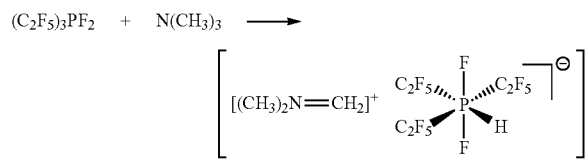

The iminium salts formed here are very reactive compounds.

For example, these compounds are intermediates in the Vilsmeier-Haack reaction, Ugi reaction, Houben-Hoesch reaction, Duff reaction and Stephen aldehyde synthesis. Iminium salts are, in addition, useful starting compounds for the synthesis of β-oxocarboxylic acid esters and β-diketones [Organikum [Practical Organic Chemistry], WILEY-VCH, 2001, p. 617] or for the synthesis of pyrrolidinium derivatives via a Cope rearrangement and intramolecular Mannich reaction [L. E. Overmann, Acc. Chem. Res., 25 (1992), p. 352-359]. Iminium salts react with alcohols (alcoholates), amines, Grignard reagents, alkyl- and aryllithium compounds, compounds containing active methyl(CH$_2$) groups, diazoalkanes (for example CH$_2$N$_2$) or 1,3-dienes.

Iminium salts are frequently used in the synthesis of amino compounds, quaternary ammonium salts, aldehydes, ketones, heterocyclic compounds or steroids [Chemical Encyclopaedia (Russ.) Vol 2, p. 418-419, Moscow, 1990].

More recent publications [T. Yamaguchi, et al., Chem and Ind., 1972, p. 380; J. of the Am. Chem. Soc., 126 (2004), p. 5968; J. of the Am. Chem. Soc., 128 (2006), p. 5648; J. of the Am. Chem. Soc., 129 (2007), p. 780; J. of the Am. Chem. Soc., 130 (2008), p. 11005; Tetrahedron, 62 (2006), p. 6312; Org. Letters, 6 (2006), p. 4093; Org. Letters, 10 (2008), p. 1417; Acc. Chem. Res., 42 (2009), p. 335; Angew. Chem. Int. Ed., 49 (2010), p. 3037] show the broad range of applications of iminium salts. The direct synthesis of these salts from tertiary or secondary amines therefore furthermore enables improvement and simplification of the preparation of a multiplicity of compounds.

Thus, for example, intermolecular rearrangements can occur starting from the iminium salts of the formula (1), where [Kt]$^{x+}$ is an iminium cation, obtained in the process according to the invention. Alternatively, the iminium salts can also react further spontaneously with the nucleophilic reagents, which is depicted by way of example in the following reaction scheme:

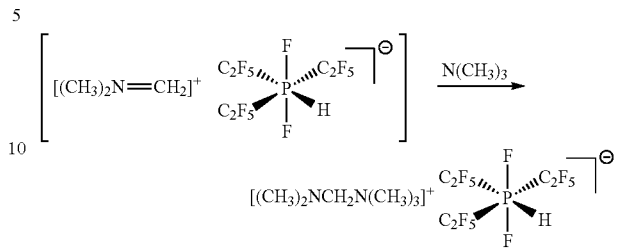

In accordance with the invention, the reaction in the first step of the process according to the invention can be carried out at −80 to 50° C. The reaction in the first step is preferably carried out at −20 to 25° C. A temperature of 0° C. is particularly preferred.

The choice of a suitable temperature for the reaction is of particular importance here in order that, in contrast to the reaction disclosed in WO 03/087113, no reduction of the substrate occurs, but instead the addition of a hydride ion takes place.

The reaction in the second step of the process according to the invention is preferably carried out at room temperature.

The reaction in the first step of the process according to the invention is preferably carried out in an aprotic solvent, such as, for example, dioxane, tetrahydrofuran, diethyl ether, methyl tert-butyl ether, hexane, cyclohexane, benzene, dichloromethane or dichloroethane. Cyclic or linear ethers, such as tetrahydrofuran, diethyl ether or methyl tert-butyl ether, are particularly preferably employed. The solvent is very particularly preferably tetrahydrofuran.

The reaction in the second step of the process according to the invention is preferably carried out in water or in a mixture of water and organic solvent.

With the aid of the process according to the invention, various salts having (perfluoroalkyl)fluorohydrogenphosphate anions can be prepared in a simple and comfortable manner. The following reaction scheme illustrates the first step of the process according to the invention with reference to the reaction of (perfluoroalkyl)fluorophosphoranes with, for example, LiAlH$_4$ as hydride ion donor:

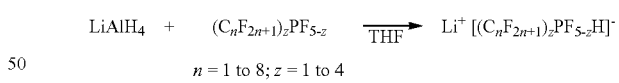

The lithium salt obtained in this way, lithium (perfluoroalkyl)fluorohydrogenphosphate (Li[(C$_n$F$_{2n+1}$)$_z$PF$_{5-z}$H]), is not only of interest for use as conductive salt (such as, for example, in Li ion batteries or in supercapacitors), but can also be used as starting material for the synthesis of various salts having organic cations (ionic liquids). This reaction represents the second step of the process according to the invention and is illustrated below by way of example:

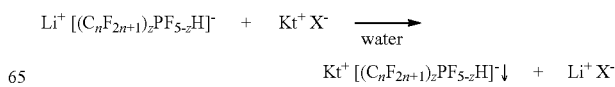

The present invention therefore likewise relates to the use of a compound of the formula (1) in which [Kt]⁺ is an inorganic cation for the preparation of a compound of the formula (1) in which [Kt]⁺ is an organic cation.

For example, ionic liquids can be prepared in this way.

The compounds of the formula (1) in which [Kt]⁺ is an organic cation which have been prepared with the aid of the process according to the invention have a multiplicity of applications:

Thus, owing to their purity, the absent vapour pressure and the high stability as solvent or solvent additive, they are suitable in chemical reactions. The use as solvent additive takes place in combination with other solvents. Furthermore, the ionic liquids according to the invention can be employed as phase-transfer catalysts, heat-exchange media, as surface-active substances, plasticisers, flameproofing agents or as conductive salts. In addition, the ionic liquids according to the invention are suitable as extractants in substance separation processes.

Owing to their electrochemical properties, the ionic liquids according to the invention can be employed, in particular, in electrochemical applications, such as, for example, as electrolyte in batteries, sensors, accumulators, capacitors or as constituent of a solar cell (solvent and/or electrolyte), preferably a dye solar cell or a sensor.

The ionic liquids prepared with the aid of the process according to the invention have modified properties, such as, for example, modified stability, compared with known ionic liquids.

These hydrophobic ionic liquids can be converted (optionally by heating) into hydrophilic ionic liquids having bis(perfluoroalkyl)phosphinate $((C_nF_{2n+1})_2P(O)O^-)$ or perfluoroalkylphosphonate anion $((C_nF_{2n+1})P(O)O_2^{-2})$ using water or caustic lye solution:

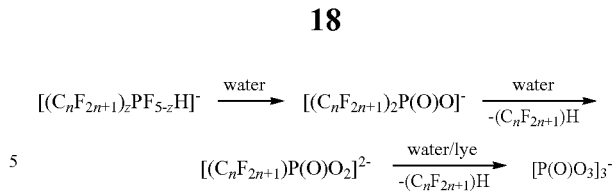

Natural products in the form of phosphates (calcium phosphate is usually formed in the environment) are thus ultimately obtained.

The present invention furthermore relates to compounds of the formula (1)

$$[Kt]^{x+}[(C_nF_{2n+1})_zPF_{5-z}H]^-_x \qquad (1)$$

in which $[Kt]^{x+}$ is an inorganic or organic cation,
where n=1-8, x=1-4 and z=1-4,
where the compounds $[(CF_3)_2PF_3H]^-K^+$, $[(CF_3)_2PF_3H]^-[(CH_3)_2NH_2]^+$, $[(CF_3)PF_4H]^-K^+$ and $[(CF_3)PF_4H]^-[(CH_3)_2NH_2]^+$ are excluded.

The cation $[Kt]^{x+}$ of the compounds of the formula (1) according to the invention can stand for an organic or inorganic cation.

In the case of an inorganic cation, this is preferably a metal cation. Particular preference is given to an alkali-metal cation, preferably a lithium, potassium or sodium cation.

Compounds according to the invention having an inorganic cation are particularly suitable as starting materials for the synthesis of compounds according to the invention having organic cations, so-called ionic liquids, as described above.

Particular preference is therefore given to compounds of the formula (1) in which $[Kt]^{x+}$ is an organic cation.

The organic cation is preferably selected from the group comprising ammonium, phosphonium, uronium, thiouronium, sulfonium, oxonium, guanidinium cations, heterocyclic cations and iminium cations, which are defined as described above.

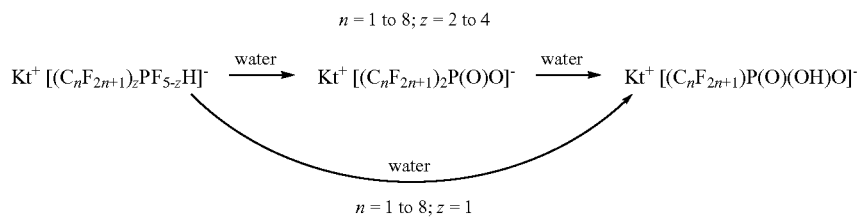

Owing to these unusual properties of the compounds according to the invention, different compounds having certain properties can be prepared as required, for example for use in extraction methods. An in situ conversion of hydrophobic ionic liquids into hydrophilic ionic liquids enables the development of a simple isolation method of water-insoluble products subsequent to a synthesis in hydrophobic ionic liquids having (perfluoroalkyl)fluorohydrogenphosphate anion.

A further difference of ionic liquids having (perfluoroalkyl)fluorohydrogenphosphate anions from other ionic liquids is their reduced stability. This can be attributed to the fact that the symmetry of the (perfluoroalkyl)fluorohydrogenphosphate anions is increased compared with the FAP anion. On hydrolysis, bis(perfluoroalkyl)phosphinates or perfluoroalkylphosphonates form, as already depicted with reference to Scheme 3. On continued hydrolysis, phosphates are formed, as depicted below:

$[Kt]^{x+}$ of the compound of the formula (1) according to the invention is particularly preferably an organic cation which is selected from the group comprising imidazolium, pyridinium, pyrrolidinium, ammonium, phosphonium, sulfonium and iminium cations, as defined above.

The organic cations $[Kt]^{x+}$ are very particularly preferably a cation selected from the group comprising phenylphosphonium, 1-ethyl-3-methylimidazolium, 1-butyl-3-methylimidazolium, N-hexylpyridinium and 1-butyl-2,3-dimethylimidazolium.

z in the compounds of the formula (1) according to the invention preferably stands for 2 or 3; z is particularly preferably =3.

In addition, n in formula (1) preferably stands for 2, 3 or 4, particularly preferably for 2 or 4. n very particularly preferably stands for 2.

The compounds of the formula (1) are particularly preferably selected from $[Kt]^{x+}[(C_2F_5)_3PF_2H]^-_x$ or $[Kt]^{x+}[(C_2F_5)_2$ $PF_3H]^-_x$, in which $[Kt]^{x+}$ stands for an organic cation selected from the group comprising ammonium, phosphonium, uronium, thiouronium, sulfonium, oxonium, guanidinium cations and heterocyclic cations, as defined above; the compounds are preferably selected from tetraphenylphosphonium difluorohydridotris(pentafluoroethyl)-phosphate, 1-ethyl-3-methylimidazolium difluorohydridotris(pentafluoroethyl)phosphate, 1-butyl-3-methylimidazolium difluorohydridotris(pentafluoroethyl)phosphate, N-hexylpyrridinium difluorohydridotris(pentafluoroethyl) phosphate, N-butyl-N-methylpyrrolidinium difluorohydridotris(pentafluoroethyl)phosphate and 1-butyl-2,3-dimethylimidazolium difluorohydridotris(pentafluoroethyl) phosphate.

As described above, the compounds according to the invention have many different properties which facilitate their use in various areas of application.

The following working examples are intended to explain the invention without limiting it. The invention can be carried out correspondingly throughout the entire range claimed. Possible variants can also be derived starting from the examples. In particular, the features and conditions of the reactions described in the examples can also be applied to other reactions which are not shown in detail, but fall within the scope of protection of the claims.

EXAMPLES

Example 1

Tetraphenylphosphonium difluorohydridotris(pentafluoroethyl)phosphate

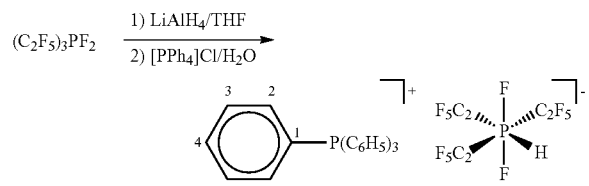

2.38 g (5.4 mmol) of $(C_2F_5)_3PF_2$ are slowly added at 0° C. to 5.6 ml of a one molar $LiAlH_4$/THF solution (5.6 mmol), and the mixture is stirred for 20 minutes. The solution is hydrolysed at 0° C. using water, giving a colourless precipitate (aluminium hydroxide), and 1.89 g (5.1 mmol) of [PPh4]Cl in 5 ml of chloroform are added. The precipitate is filtered off and washed with chloroform. The aqueous phase is separated off, and the chloroform phase is dried in vacuo, leaving a colourless precipitate.

Yield (based on [PPh4]Cl): 3.18 g (78%)

Melting point: 114-116° C.

TABLE 1.1

$^{19}$F-NMR data of $[PPh_4][P(C_2F_5)_3F_2H]$ in $CDCl_3$

| δ [ppm] | Multiplicity | J [Hz] | Assignment | Integral |
|---|---|---|---|---|
| −81.4 | m | — | trans-$CF_3$ | 1.6 |
| −83.1 | m | — | cis-$CF_3$ | 3.3 |
| −113.9 | d, d, m | $^1J_{(PF)} = 737$ <br> $^2J_{(FH)} = 58$ | PF | 1 |
| −120.6 | d, m | $^2J_{(PF)} = 104$ | trans-$CF_2$ | 1 |
| −127.3 | d, m | $^2J_{(PF)} = 93$ | cis-$CF_2$ | 2 |

TABLE 1.2

$^{31}$P-NMR data of $[PPh_4][P(C_2F_5)_3F_2H]$ in $CDCl_3$

| δ [ppm] | Multiplicity | J [Hz] | Assignment | Integral |
|---|---|---|---|---|
| 23.4 | s | — | $[PPh_4][(C_2F_5)_3PF_2H]$ | 1 |
| −154.9 | d, t, quin, t | $^1J_{(PF)} = 738$ <br> $^2J_{(PFtrans)} = 104$ <br> $^2J_{(PFcis)} = 93$ <br> $^1J_{(PH)} = 678$ | $[PPh_4][(C_2F_5)_3PF_2H]$ | 0.9 |

TABLE 1.3

$^1$H-NMR data of $[PPh_4][P(C_2F_5)_3F_2H]$ in $CDCl_3$

| δ [ppm] | Multiplicity | J [Hz] | Assignment | Integral |
|---|---|---|---|---|
| 5.6 | d, t, t, m | $^1J_{(PH)} = 678$ <br> $^2J_{(HF)} = 64$ <br> $^3J_{(HFtrans)} = 13$ | $[(C_2F_5)_3PF_2H]^-$ | 1 |
| 7.6-7.9 | m | — | $[P(C_6H_5)_4]^+$ | 25 |

TABLE 1.4

Elemental analysis data

| | C | H |
|---|---|---|
| calculated | 47.01 | 2.76 |
| experimental | 47.15 | 2.87 |

TABLE 1.5

Mass-spectrometric data (EI, 20 eV)

| m/e | Rel. intensity [%] | Assignment |
|---|---|---|
| 672 | 1 | $[PPh_3(C_2F_5)_3PFH]^+$ |
| 628 | 0 | $[PPh_4(C_2F_5)_2PH]^+$ |
| 596 | 2 | $[PPh_4(C_2F_5)(CF_3)PF_2]^+$ |
| 566 | 1 | $[PPh_3(C_2F_5)_2PF_2]^+$ |
| 551 | 0 | $[PPh_3(C_2F_5)_2PH]^+$ |
| 520 | 2 | $[PPh_3(C_2F_5)(CF_3)PF_2]^+$ |
| 490 | 4 | $[PPh_2(C_2F_5)_2PF_2]^+$ |
| 444 | 2 | $[PPh(C_2F_5)(CF_3)PF_2]^+$ |
| 414 | 13 | $[PPh(C_2F_5)_2PF_2]^+$ |
| 355 | 6 | $[PPh_2(C_2F_5)PF]^+$ |
| 337 | 53 | $[PPh_4]^+$ |
| 277 | 7 | $[PPh(C_2F_5)PF]^+$ |
| 262 | 100 | $[PPh_3]^+$ |
| 183 | 23 | $[(C_2F_5)PFH]^+$ |
| 108 | 7 | $[PPh]^+$ |
| 78 | 9 | $[Ph]^+$ |

TABLE 1.6

ESI mass spectrum - negative scan mode

| Signal | Rel. intensity [%] | Assignment |
|---|---|---|
| 307.18 | 19 | $[(C_2F_5)_2PF_2]^-$ |
| 417.21 | 100 | $[(C_2F_5)_3PF_2H]^-$ |

Example 2

1-Ethyl-3-methylimidazolium difluorohydridotris-(penta-fluoroethyl)phosphate, [EMIM][P(C$_2$F$_5$)$_3$F$_2$H]

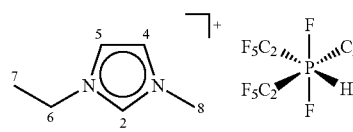

8.1 g (19 mmol) of (C$_2$F$_5$)$_3$PF$_2$ are slowly added at 0° C. to 20 ml of a one molar LiAlH$_4$/THF solution (20 mmol), and the mixture is stirred for 30 minutes. The solution is hydrolysed using water at 0° C., giving a colourless precipitate (aluminium hydroxide), and 2.8 g (19 mmol) of 1-ethyl-3-methylimidazolium chloride, dissolved in 2 ml of water, are added. After stirring for 30 minutes, the precipitate is filtered off. A second phase deposits, which is separated off and extracted twice with water. It is subsequently dried in vacuo, leaving a colourless liquid.

Yield (based on 1-ethyl-3-methylimidazolium chloride): 3.4 g (33%)

Analytical data of [EMIM][P(C$_2$F$_5$)$_3$F$_2$H]:

| | |
|---|---|
| Melting point [° C.] | −2.4 |
| Decomposition [° C.] | 176 |
| H$_2$O content [ppm] | 43 |
| Cl$^-$ content [ppm] | <5 |
| F$^-$ content [ppm] | 112 |

TABLE 2.1

$^{19}$F-NMR data of [EMIM][P(C$_2$F$_5$)$_3$F$_2$H] in acetone-d$_6$

| δ [ppm] | Multiplicity | J [Hz] | Assignment | Integral |
|---|---|---|---|---|
| −81.1 | m, d | $^4J_{(FH)} = 1$ | trans-CF$_3$ | 1 |
| −82.3 | quin, d | $^3J_{(PF)} = 9$<br>$^4J_{(FH)} = 2$ | cis-CF$_3$ | 2 |
| −114.1 | d, d, m | $^1J_{(PF)} = 736$<br>$^2J_{(FH)} = 64$ | PF | 0.7 |
| −119.7 | d, m | $^2_{(PF)} = 104$ | trans-CF$_2$ | 0.6 |
| −126.3 | d, m | $^2J_{(PF)} = 93$ | cis-CF$_2$ | 1.2 |

TABLE 2.2

$^{31}$P-NMR data of [EMIM][P(C$_2$F$_5$)$_3$F$_2$H] in acetone-d$_6$

| δ [ppm] | Multiplicity | J [Hz] | Assignment |
|---|---|---|---|
| −154.4 | d, t, quin, t | $^1J_{(PF)} = 735$<br>$^1J_{(PH)} = 678$<br>$^2J_{(PFtrans)} = 104$<br>$^2J_{(PFcis)} = 93$ | [(C$_2$F$_5$)$_3$PF$_2$H]$^-$ |

TABLE 2.3

$^1$H-NMR data of [EMIM][P(C$_2$F$_5$)$_3$F$_2$H] in acetone-d$_6$

| δ [ppm] | Multiplicity | J [Hz] | Assignment | Integral |
|---|---|---|---|---|
| 1.6 | t | $^3J_{(HH)} = 7$ | H7 | 3 |
| 4.0 | s | — | H8 | 3 |
| 4.4 | q | $^3J_{(HH)} = 7$ | H6 | 2 |
| 5.7 | d, t, t, m | $^1J_{(PH)} = 675$<br>$^2J_{(HF)} = 63$<br>$^3J_{(HFtrans)} = 13$ | [(C$_2$F$_5$)$_3$PF$_2$H]$^-$ | 1 |
| 7.7/7.8 | t | $^3J_{(HH)} = 2$ | H4/5 | 2 |
| 9.0 | s | — | H2 | 1 |

TABLE 2.4

$^{13}$C{$^1$H}-NMR data of [EMIM][P(C$_2$F$_5$)$_3$F$_2$H] in acetone-d$_6$

| δ [ppm] | Multiplicity | J [Hz] | Assignment |
|---|---|---|---|
| 14.5 | s | — | C7 |
| 35.6 | s | — | C8 |
| 44.9 | s | — | C6 |
| 119.9 | m | — | —CF$_2$CF$_3$ |
| 122.2 | s | — | C5 |
| 122.9 | m | — | —CF$_2$CF$_3$ |
| 123.9 | s | — | C4 |
| 136.2 | s | — | C2 |

$^a${$^1$H}
$^b${$^{19}$F}

Example 3

1-Butyl-3-methylimidazolium difluorohydridotris(pentafluoroethyl)phosphate, [BMIM][P(C$_2$F$_5$)$_3$F$_2$H]

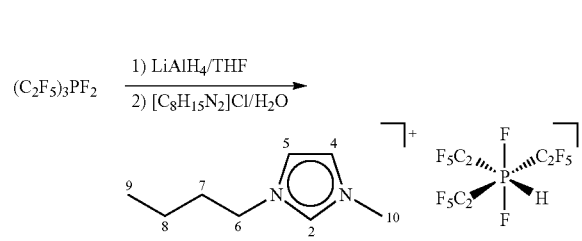

12.1 g (28.5 mmol) of (C$_2$F$_5$)$_3$PF$_2$ are slowly added at 0° C. to 30 ml of a one molar LiAlH$_4$/THF solution (30 mmol), and the mixture is stirred for 30 minutes. The solution is hydrolysed using water at 0° C., giving a colourless precipitate (aluminium hydroxide), and 4.9 g (28.5 mmol) of 1-butyl-3-methylimidazolium chloride in water are added. After stirring for 20 minutes, the precipitate is filtered off. A second phase deposits, which is separated off and extracted twice with water. It is subsequently dried in vacuo, leaving a colourless viscous liquid.

Yield (based on 1-butyl-3-methylimidazolium chloride): 10.2 g (64%)

Analytical data of [BMIM][P(C$_2$F$_5$)$_3$F$_2$H]:

| | |
|---|---|
| Glass transition [° C.] | −86 |
| Cold crystallisation [° C.] | −38 |
| Melting point [° C.] | −2.6 |
| Decomposition [° C.] | 177 |
| H$_2$O content [ppm] | 40 |
| Cl$^-$ content [ppm] | <5 |
| F$^-$ content [ppm] | 48 |

Viscosity and density of [BMIM][P(C$_2$F$_5$)$_3$F$_2$H]:

| T [° C.] | ν [mm$^2$/s] | ρ [g/cm$^3$] |
|---|---|---|
| 20 | 96.48 | 1.581 |
| 30 | 58.94 | 1.571 |
| 40 | 38.64 | 1.560 |
| 50 | 26.78 | 1.549 |
| 60 | 19.45 | 1.538 |
| 70 | 14.65 | 1.527 |
| 80 | 11.38 | 1.517 |

TABLE 3.1

$^{19}$F-NMR data of [BMIM][P(C$_2$F$_5$)$_3$F$_2$H] in acetone-d$_6$

| δ [ppm] | Multiplicity | J [Hz] | Assignment | Integral |
|---|---|---|---|---|
| −80.8 | m | — | trans-CF$_3$ | 1 |
| −81.9 | m | — | cis-CF$_3$ | 1.9 |
| −115.0 | d, d, m | $^1J_{(PF)}$ = 724<br>$^2J_{(FH)}$ = 65 | PF | 0.6 |
| −119.1 | d, m | $^2J_{(PF)}$ = 107 | trans-CF$_2$ | 0.6 |
| −125.7 | d, m | $^2J_{(PF)}$ = 92 | cis-CF$_2$ | 1.3 |

TABLE 3.2

$^{31}$P-NMR data of [BMIM][P(C$_2$F$_5$)$_3$F$_2$H] in acetone-d$_6$

| δ [ppm] | Multiplicity | J [Hz] | Assignment |
|---|---|---|---|
| −154.2 | d, t, quin, t | $^1J_{(PF)}$ = 737<br>$^1J_{(PH)}$ = 676<br>$^2J_{(PFtrans)}$ = 104<br>$^2J_{(PFcis)}$ = 94 | [C$_2$F$_5$)$_3$PF$_2$H]$^-$ |

TABLE 3.3

$^1$H-NMR data of [BMIM][P(C$_2$F$_5$)$_3$F$_2$H] in acetone-d$_6$

| δ [ppm] | Multiplicity | J [Hz] | Assignment | Integral |
|---|---|---|---|---|
| 0.9 | t | $^3J_{(HH)}$ = 7 | H9 | 3.1 |
| 1.4 | sext | $^3J_{(HH)}$ = 8 | H8 | 2.1 |
| 1.9 | quin | $^3J_{(HH)}$ = 7 | H7 | 2.2 |
| 4.0 | s | — | H10 | 3.1 |
| 4.4 | t | $^3J_{(HH)}$ = 8 | H6 | 2 |
| 5.7 | d, t, t, m | $^1J_{(PH)}$ = 675<br>$^2J_{(HF)}$ = 63<br>$^3J_{(HFtrans)}$ = 13 | [(C$_2$F$_5$)$_3$PF$_2$H]$^-$ | 0.6 |
| 7.7 | m | $^3J_{(HH)}$ = 7 | H4, H5 | 2 |
| 9.1 | s | — | H2 | 1 |

TABLE 3.4

$^{13}$C{$^1$H}-NMR data of [BMIM][P(C$_2$F$_5$)$_3$F$_2$H] in acetone-d$_6$

| δ [ppm] | Multiplicity | J [Hz] | Assignment |
|---|---|---|---|
| 12.7 | s | — | C9 |
| 19.0 | s | — | C8 |
| 31.8 | s | — | C7 |
| 35.7 | s | — | C6 |
| 49.4 | s | — | C10 |
| 118.9 | m | — | —CF$_2$CF$_3$ |
| 122.5 | s | — | C4 |
| 122.9 | m | — | —CF$_2$CF$_3$ |
| 123.9 | s | — | C5 |
| 136.4 | s | — | C2 |

$^a${$^1$H}
$^b${$^{19}$F}

Example 4

N-Hexylpyrridinium difluorohydridotris(pentafluoroethyl)phosphate, [HPy][P(C$_2$F$_5$)$_3$F$_2$H]

$$(C_2F_5)_3PF_2 \xrightarrow[\text{2) } [C_{11}H_{18}N]Cl/H_2O]{\text{1) LiAlH}_4/\text{THF}}$$

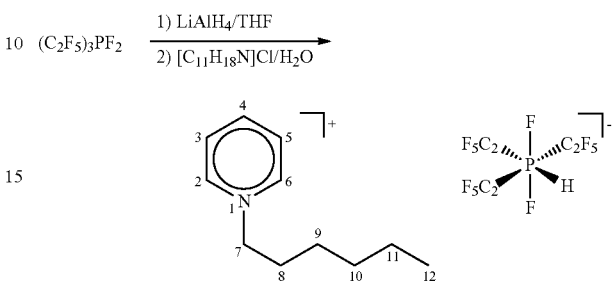

12.14 g (28.5 mmol) of (C$_2$F$_5$)$_3$PF$_2$ are slowly added at 0° C. to 30 ml of a one molar LiAlH$_4$/THF solution (30 mmol), and the mixture is stirred for 30 minutes. The solution is hydrolysed using water at 0° C., giving a colourless precipitate (aluminium hydroxide), and 5.67 g (28.5 mmol) of N-hexylpyrridinium chloride, dissolved in 10 ml of water, are added. After stirring for 30 minutes, the precipitate is filtered off. The emulsion obtained is dried in vacuo. The cloudy, viscous residue is extracted three times with water and again dried in vacuo, leaving a colourless liquid.

Yield (based on N-hexylpyrridinium chloride): 9.98 g (59%)

Analytical data of [HPy][P(C$_2$F$_5$)$_3$F$_2$H]

| Glass transition [° C.] | −76 |
|---|---|
| Decomposition [° C.] | 166 |
| H$_2$O content [ppm] | 27 |
| Cl$^-$ content [ppm] | 143 |

TABLE 4.1

$^{19}$F-NMR data of [HPy][P(C$_2$F$_5$)$_3$F$_2$H] in acetone-d$_6$

| δ [ppm] | Multiplicity | J [Hz] | Assignment | Integral |
|---|---|---|---|---|
| −79.9 | m | — | trans-CF$_3$ | 1 |
| −81.1 | m | — | cis-CF$_3$ | 2 |
| −112.9 | d, d, m | $^1J_{(PF)}$ = 737<br>$^2J_{(FH)}$ = 61 | PF | 0.6 |
| −118.6 | d, m | $^2J_{(PF)}$ = 105 | trans-CF$_2$ | 0.5 |
| −125.2 | d, m | $^2J_{(PF)}$ = 92 | cis-CF$_2$ | 1.2 |

TABLE 4.2

$^{31}$P-NMR data of [HPy][P(C$_2$F$_5$)$_3$F$_2$H] in acetone-d$_6$

| δ [ppm] | Multiplicity | J [Hz] | Assignment |
|---|---|---|---|
| −152.7 | d, t, quin, t | $^1J_{(PF)}$ = 737<br>$^1J_{(PH)}$ = 676<br>$^2J_{(PFtrans)}$ = 104<br>$^2J_{(PFcis)}$ = 94 | [C$_2$F$_5$)$_3$PF$_2$H]$^-$ |

TABLE 4.3

$^1$H-NMR data of [HPy][P(C$_2$F$_5$)$_3$F$_2$H] in acetone-d$_6$

| δ [ppm] | Multiplicity | J [Hz] | Assignment | Integral |
|---|---|---|---|---|
| 0.9 | m | — | H12 | 3 |
| 1.3; 1.9 | m | — | H8–H11 | 9 |
| 4.5 | t | $^3J_{(HH)} = 7$ | H7 | 2 |
| 5.6 | d, t, t, m | $^1J_{(PH)} = 673$  $^2J_{(HF)} = 63$  $^3J_{(HFtrans)} = 13$ | [(C$_2$F$_5$)$_3$PF$_2$H]$^-$ | 1 |
| 8.0 | m | — | H3, H5 | 2 |
| 8.5 | t | $^3J_{(HH)} = 8$ | H4 | 1 |
| 8.7 | d | $^3J_{(HH)} = 6$ | H2, H6 | 2 |

TABLE 4.4

$^{13}$C-{$^1$H}-NMR data of [HPy][P(C$_2$F$_5$)$_3$F$_2$H] in acetone-d$_6$

| δ [ppm] | Multiplicity | J [Hz] | Assignment |
|---|---|---|---|
| 13.1 | s | — | C12 |
| 22.0 | s | — | C11 |
| 25.2 | s | — | C10 |
| 30.7 | s | — | C9 |
| 30.8 | s | — | C8 |
| 61.9 | s | — | C7 |
| 118.2 | m | — | —CF$_2$CF$_3$ |
| 120.9 | m | — | —CF$_2$CF$_3$ |
| 128.4 | s | — | C4 |
| 144.4 | s | — | C3, C5 |
| 145.7 | s | — | C2, C6 |

$^a${$^1$H}
$^b${$^{19}$F}

Example 5

1-Butyl-2,3-dimethylimidazolium difluorohydridotris(pentafluoroethyl)phosphate, [BMMIM][P(C$_2$F$_5$)$_3$F$_2$H]

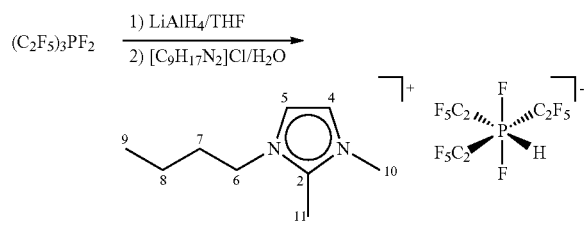

12.1 g (28.5 mmol) of (C$_2$F$_5$)$_3$PF$_2$ are slowly added at 0° C. to 30 ml of a one molar LiAlH$_4$/THF solution (30 mmol), and the mixture is stirred for 30 minutes. The solution is hydrolysed using water at 0° C., giving a colourless precipitate (aluminium hydroxide), and 5.4 g (28.5 mmol) of 1-butyl-2,3-dimethylimidazolium chloride, dissolved in 2 ml of water, are added. After stirring for 20 minutes, the precipitate is filtered off. A second phase deposits, which is separated off and extracted twice with water. It is subsequently dried in vacuo, leaving a colourless liquid.

Yield (based on 1-butyl-2,3-dimethylimidazolium chloride): 9.1 g (55%)

Analytical data of [BMMIM][P(C$_2$F$_5$)$_3$F$_2$H]:

| Glass transition [° C.] | −78 |
|---|---|
| Cold crystallisation [° C.] | −24 |
| Melting point [° C.] | 9.6 |
| Decomposition [° C.] | 179 |
| H$_2$O content [ppm] | 122 |
| Cl$^-$ content [ppm] | 6 |
| F$^-$ content [ppm] | 198 |

TABLE 5.1

$^{19}$F-NMR data of [BMMIM][P(C$_2$F$_5$)$_3$F$_2$H] in acetone-d$_6$

| δ [ppm] | Multiplicity | J [Hz] | Assignment | Integral |
|---|---|---|---|---|
| −79.9 | m | — | trans-CF$_3$ | 1 |
| −81.1 | m | — | cis-CF$_3$ | 2 |
| −112.9 | d, d, m | $^1J_{(PF)} = 737$  $^2J_{(FH)} = 65$ | PF | 0.7 |
| −118.6 | d, m | $^2J_{(PF)} = 105$ | trans-CF$_2$ | 0.6 |
| −125.1 | d, m | $^2J_{(PF)} = 95$ | cis-CF$_2$ | 1.2 |

TABLE 5.2

$^{31}$P-NMR data of [BMMIM][P(C$_2$F$_5$)$_3$F$_2$H] in acetone-d$_6$

| δ [ppm] | Multiplicity | J [Hz] | Assignment |
|---|---|---|---|
| −153.7 | d, t, quin, t | $^1J_{(PF)} = 737$  $^1J_{(PH)} = 674$  $^2J_{(PFtrans)} = 104$  $^2J_{(PFcis)} = 92$ | [C$_2$F$_5$)$_3$PF$_2$H]$^-$ |

TABLE 5.3

$^1$H-NMR data of [BMMIM][P(C$_2$F$_5$)$_3$F$_2$H] in acetone-d$_6$

| δ [ppm] | Multiplicity | J [Hz] | Assignment | Integral |
|---|---|---|---|---|
| 1.0 | t | $^3J_{(HH)} = 7$ | H9 | 1.5 |
| 1.4 | sext | $^3J_{(HH)} = 7$ | H8 | 1 |
| 1.9 | quin | $^3J_{(HH)} = 7$ | H7 | 1 |
| 2.8 | s | — | H11 | 1.5 |
| 3.9 | s | — | H10 | 1.6 |
| 4.3 | t | $^3J_{(HH)} = 7$ | H6 | 1.1 |
| 5.7 | d, t, t, m | $^1J_{(PH)} = 675$  $^2J_{(HF)} = 63$  $^3J_{(HFtrans)} = 13$ | [(C$_2$F$_5$)$_3$PF$_2$H]$^-$ | — |
| 7.6 | m | — | H4, H5 | 1 |

TABLE 5.4

$^{13}$C-{$^1$H}-NMR data of [BMMIM][P(C$_2$F$_5$)$_3$F$_2$H] in acetone-d$_6$

| δ [ppm] | Multiplicity | J [Hz] | Assignment |
|---|---|---|---|
| 8.9 | s | — | C11 |
| 12.7 | s | — | C9 |
| 19.1 | s | — | C8 |
| 31.2 | s | — | C7 |
| 34.6 | s | — | C10 |
| 48.0 | s | — | C6 |
| 120.8 | s | — | C4/5 |
| 122.2 | s | — | C4/5 |
| 144.4 | s | — | C2 |

Example 6

Hydrolysis of [EMIm][P(C₂F₅)₃F₂H]

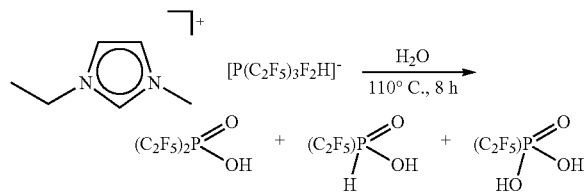

0.72 g of [EMIm][P(C₂F₅)₃PF₂H] are stirred at 110° C. for 8 hours in 10 ml of H₂O. Volatile constituents are subsequently removed in vacuo, and the residue is investigated by NMR spectroscopy.

TABLE 6.1

$^{31}$P-NMR spectroscopic data of the residue in H₂O

| δ [ppm] | Multiplicity | J[Hz] | Assignment |
|---|---|---|---|
| 5.4 | d, t | $^1J_{(PH)}$ = 586<br>$^2J_{(PF)}$ = 80 | (C₂F₅)PH(O)OH |
| 2.3 | quin | $^2J_{(PF)}$ = 76 | (C₂F₅)₂P(O)OH |
| −3.5 | t | $^2J_{(PF)}$ = 78 | (C₂F₅)P(O)(OH)₂ |

Example 7

Synthesis of [Me₂NCH₂NMe₃][P(C₂F₅)₃F₂H]

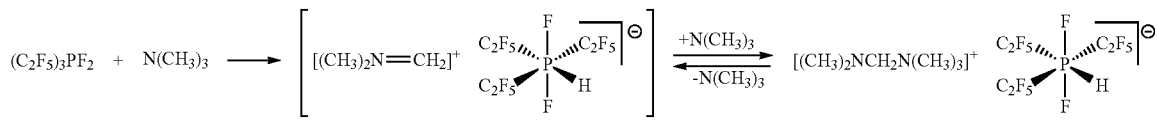

0.43 g (7.3 mmol) of trimethylamine, NMe₃, are condensed into 5.14 g (12.1 mmol) of tris(pentafluoethyl)difluorophosphorane, (C₂F₅)₃PF₂. The mixture is brought to room temperature, whereupon two phases can be observed. The mixture is subsequently stirred at room temperature for 24 hours. After a few hours, a colourless solid forms. After one day, volatile substances are removed in vacuo, leaving a colourless solid. Yield of the crude product (based on NMe₃) is virtually quantitative (1.99 g).

TABLE 7.1

$^{31}$P-NMR data of [(CH₃)₂NCH₂N(CH₃)₃][P(C₂F₅)₃F₂H] in CD₃CN

| δ, ppm | Multiplicity | J/Hz | Assignment |
|---|---|---|---|
| −153.7 | d, t, quin, t | $^1J_{(PH)}$ = 674<br>$^1J_{(PF)}$ = 733<br>$^2J_{(PFcis)}$ = 94<br>$^2J_{(PFtrans)}$ = 104 | [P(C₂F₅)₃F₂H]⁻ |

TABLE 7.2

$^{19}$F-NMR data of [(CH₃)₂NCH₂N(CH₃)₃][P(C₂F₅)₃F₂H] in CD₃CN

| δ, ppm | Multiplicity | J/Hz | Assignment | Integral |
|---|---|---|---|---|
| −80.6 | m | — | trans-CF₃ | 3 |
| −81.8 | m | — | cis-CF₃ | 6 |
| −113.6 | d, d, m, | $^1J_{(PF)}$ = 733<br>$^2J_{(FH)}$ = 62 | PF | 2 |
| −119.1 | d, m | $^2J_{(PFtrans)}$ = 104 | trans-CF₂ | 2 |
| −125.7 | d, m | $^2J_{(PFcis)}$ = 94 | cis-CF₂ | 4 |

TABLE 7.3

$^1$H-NMR spectroscopic data of [(CH₃)₂NCH₂N(CH₃)₃][P(C₂F₅)₃F₂H] in CD₃CN

| δ, ppm | Multiplicity | J/Hz | Assignment | Integral |
|---|---|---|---|---|
| 2.6 | s | — | (CH₃)₂N— | 6 |
| 2.8 | s | — | —N(CH₃)₃ | 9 |
| 4.0 | s | — | —NCH₂N— | 2 |
| 5.7 | d, t, m | $^1J_{(PH)}$ = 675<br>$^2J_{(FH)}$ = 63 | [P(C₂F₅)₃PF₂H]⁻ | 1 |

TABLE 7.4

$^{13}$C{$^1$H}-NMR spectroscopic data of [(CH₃)₂NCH₂N(CH₃)₃][P(C₂F₅)₃F₂H] in CD₃CN

| δ, ppm | Multiplicity | J/Hz | Assignment | Integral |
|---|---|---|---|---|
| 45.3 | s | — | (CH₃)₂N— | |
| 48.4 | s | — | —N(CH₃)₃ | |
| 90.5 | s | — | —NCH₂N— | |

Example 8

Reaction of N(C₂H₅)₃ with (C₂F₅)₃PF₂

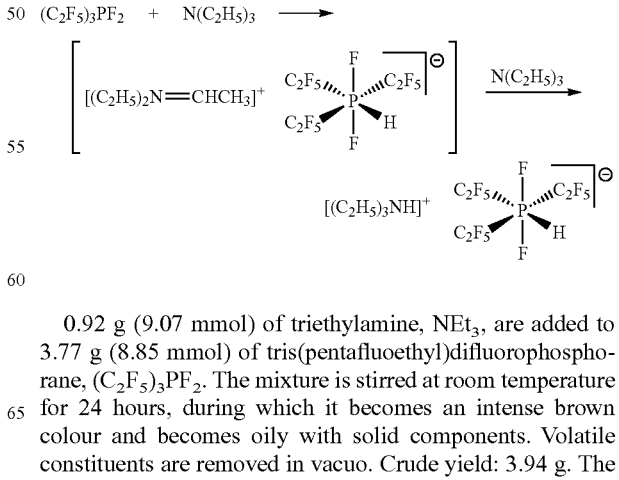

0.92 g (9.07 mmol) of triethylamine, NEt₃, are added to 3.77 g (8.85 mmol) of tris(pentafluoethyl)difluorophosphorane, (C₂F₅)₃PF₂. The mixture is stirred at room temperature for 24 hours, during which it becomes an intense brown colour and becomes oily with solid components. Volatile constituents are removed in vacuo. Crude yield: 3.94 g. The crude product is dissolved in $CH_2Cl_2$, and the product, $[(C_2H_5)_3NH]-[P(C_2F_5)_3F_2H]$, is brought to crystallisation at $-28°$ C.

IR(ATR): v(NH) 3203 $cm^{-1}$

TABLE 8.1

$^{31}P$-NMR data of $[(C_2H_5)_3NH][P(C_2F_5)_3F_2H]$ in $CD_3CN$

| δ, ppm | Multiplicity | J/Hz | Assignment |
|---|---|---|---|
| −152.6 | d, t, quin, t | $^1J_{(PH)} = 681$<br>$^1J_{(PF)} = 723$<br>$^2J_{(PFtrans)} = 107$<br>$^2J_{(PFcis)} = 92$ | $[P(C_2F_5)_3F_2H]^-$ |

TABLE 8.2

$^{19}F$-NMR data of $[(C_2H_5)_3NH][P(C_2F_5)_3F_2H]$ in $CD_3CN$

| δ, ppm | Multiplicity | J/Hz | Assignment | Integral |
|---|---|---|---|---|
| −81.0 | m | — | trans-$CF_3$ | 3 |
| −82.2 | "quin", d | 8.5/1 | cis-$CF_3$ | 6 |
| −115.3 | d, d, m | $^1J_{(PF)} = 719$<br>$^2J_{(HF)} = 62$ | $[P(C_2F_5)_3F_2H]^-$ | 2 |
| −119.2 | d, m | $^2J_{(PF)} = 107$ | trans-$CF_2$ | 2 |
| −125.8 | d, m | $^2J_{(PF)} = 95$ | cis-$CF_2$ ($[P(C_2F_5)_3F_2H]^-$) | 4 |

TABLE 8.3

$^1H$-NMR data of $[(C_2H_5)_3NH][P(C_2F_5)_3F_2H]$ in $CD_3CN$

| δ, ppm | Multiplicity | J/Hz | Assignment | Integral |
|---|---|---|---|---|
| 1.3 | t | $^3J_{(HH)} = 7$ | —$CH_3$ | 9 |
| 3.2 | quar | $^3J_{(HH)} = 7$ | —$CH_2$— | 6 |
| 5.7 | d, quin, t, m | $^1J_{(PH)} = 645$<br>$^3J_{(FH)} = 13$<br>$^3J_{(FH)} = 2$ | $[P(C_2F_5)_3F_2H]^-$ | 1 |

TABLE 8.4

$^{13}C\{^1H\}$-NMR data of $[(C_2H_5)_3NH][P(C_2F_5)_3F_2H]$ in $CD_3CN$

| δ, ppm | Multiplicity | J/Hz | Assignment |
|---|---|---|---|
| 8.2 | s | — | —$CH_3$ |
| 47.0 | s | — | —$CH_2$— |

Example 9

Reaction of $HN(C_2H_5)_2$ with $(C_2F_5)_3PF_2$

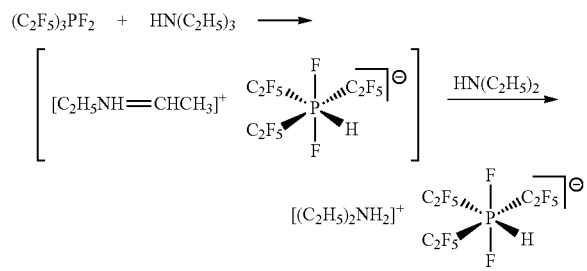

0.60 g (8.25 mmol) of diethylamine, $HNEt_2$, are added to 3.44 g (8.08 mmol) of tris(pentafluoethyl)difluorophosphorane, $(C_2F_5)_3PF_2$. The mixture is stirred at room temperature for 24 hours, during which it becomes an intense brown colour. Volatile constituents are removed in vacuo. Crude yield: 3.18 g.

The crude product is dissolved in $CH_2Cl_2$, and the product, $[(C_2H_5)_2NH_2]-[P(C_2F_5)_3F_2H]$, is brought to crystallisation at $-28°$ C.

TABLE 9.1

$^{31}P$-NMR data of $[(C_2H_5)_2NH_2][P(C_2F_5)_3F_2H]$ in $CD_3CN$

| δ, ppm | Multiplicity | J/Hz | Assignment |
|---|---|---|---|
| −153.2 | d, t, quin, t | $^1J_{(PH)} = 679$<br>$^1J_{(PF)} = 721$<br>$^2J_{(PFcis)} = 92$<br>$^2J_{(PFtrans)} = 106$ | $[P(C_2F_5)_3F_2H]^-$ |

TABLE 9.2

$^{19}F$-NMR data of $[(C_2H_5)_2NH_2][P(C_2F_5)_3F_2H]$ in $CD_3CN$

| δ, ppm | Multiplicity | J/Hz | Assignment | Integral |
|---|---|---|---|---|
| −81.5 | m | — | trans-$CF_3$ | — |
| −82.8 | m | — | cis-$CF_3$ | — |
| −114.9 | d, d, m | $^1J_{(PF)} = 722$<br>$^2J_{(HF)} = 65$ | $[P(C_2F_5)_3F_2H]^-$ | 2 |
| −119.3 | d, m | $^2J_{(PFtrans)} = 105$ | trans-$CF_2$ | 2 |
| −126.0 | d, m | $^2J_{(PFcis)} = 92$ | cis-$CF_2$ | 4 |

TABLE 9.3

$^1H$-NMR data of $[(C_2H_5)_2NH_2][P(C_2F_5)_3F_2H]$ in $CD_2Cl_2$

| δ, ppm | Multiplicity | J/Hz | Assignment | Integral |
|---|---|---|---|---|
| 1.4 | t | 7 | —$CH_3$ | 1.5 |
| 3.1 | quar | 7 | —$CH_2$— | 1 |
| 5.8 | d, t, quin, m | $^1J_{(PH)} = 681$<br>$^2J_{(HF)} = 63$<br>$^3J_{(HFcis)} = 14$ | $[P(C_2F_5)_3F_2H]^-$ | 0.15 |

TABLE 9.4

$^{13}C\{^1H\}$-NMR data of $[(C_2H_5)_2NH_2][P(C_2F_5)_3F_2H]$ in $CD_2Cl_2$

| δ, ppm | Multiplicity | J/Hz | Assignment |
|---|---|---|---|
| 10.9 | s | — | —$CH_3$ |
| 43.6 | s | — | —$CH_2$— |

Example 10

Reaction of Me$_2$NCH$_2$NMe$_2$ with (C$_2$F$_5$)$_3$PF$_2$

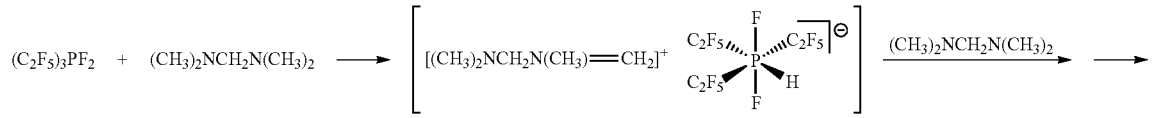

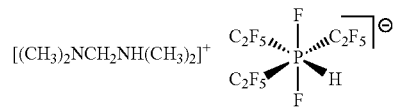

4.5 g (10.6 mmol) of tris(pentafluoethyl)difluorophosphorane, (C$_2$F$_5$)$_3$PF$_2$, are added at room temperature to 0.88 g (8.6 mmol) of Me$_2$NCH$_2$NMe$_2$. Two phases can be observed. The mixture is stirred for 24 hours, during which a yellow emulsion forms. Excess (C$_2$F$_5$)$_3$PF$_2$ is removed in vacuo, and the residue is investigated by NMR spectroscopy.

IR(ATR): ν(NH) 3202 cm$^{-1}$

TABLE 10.1

$^{31}$P-NMR data of the [P(C$_2$F$_5$)$_3$F$_2$H] anion in CD$_3$CN

| δ, ppm | Multiplicity | J/Hz | Assignment |
|---|---|---|---|
| −154.1 | d, t, quin, m | $^1J_{(PH)}$ = 678<br>$^1J_{(PF)}$ = 730<br>$^2J_{(PFcis)}$ = 93 | [P(C$_2$F$_5$)$_3$F$_2$H]$^-$ |

TABLE 10.2

$^{19}$F-NMR data of the [P(C$_2$F$_5$)$_3$F$_2$H] anion in CD$_3$CN

| δ, ppm | Multiplicity | J/Hz | Assignment |
|---|---|---|---|
| −81.1 | m | — | trans-CF$_3$ |
| −82.4 | m | — | cis-CF$_3$ |
| −113.2 | d, d, m | $^1J_{(PF)}$ = 724<br>$^2J_{(HF)}$ = 68 | [P(C$_2$F$_5$)$_3$F$_2$H]$^-$ |
| −119.3 | d, m | $^2J_{(PFtrans)}$ = 118 | trans-CF$_2$ |
| −125.7 | d, m | $^2J_{(PFcis)}$ = 94 | cis-CF$_2$ |

Example 11

Reaction of i-(C$_3$H$_7$)$_2$NCH$_3$ with (C$_2$F$_5$)$_3$PF$_2$

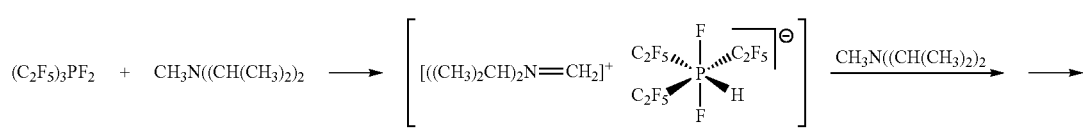

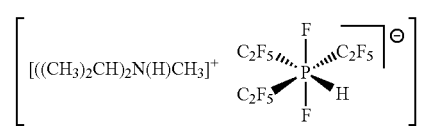

0.82 g (7.12 mmol) of N,N-diisopropylmethylamine are dissolved in 50 ml of diethyl ether, and 3.03 g (7.0 mmol) of tris(pentafluoethyl)difluorophosphorane, (C$_2$F$_5$)$_3$PF$_2$, are added at room temperature. The mixture is stirred for four days and subsequently freed from volatile substances in vacuo, leaving a brown solid, which is purified by recrystallisation from CH$_2$Cl$_2$ at −28° C., leaving a colourless solid. Yield: 2.61 g.

TABLE 11.1

$^{31}$P-NMR data of [((CH$_3$)$_2$CH)$_2$N(H)CH$_3$][P(C$_2$F$_5$)$_3$F$_2$H] in CD$_3$CN

| δ, ppm | Multiplicity | J/Hz | Assignment |
|---|---|---|---|
| −154.4 | d, t, quin, t | $^1J_{(PH)}$ = 675<br>$^1J_{(PF)}$ = 733<br>$^2J_{(PFtrans)}$ = 104<br>$^2J_{(PFcis)}$ = 94 | [P(C$_2$F$_5$)$_3$F$_2$H]$^-$ |

TABLE 11.2

$^{19}$F-NMR data of [((CH$_3$)$_2$CH)$_2$N(H)CH$_3$][P(C$_2$F$_5$)$_3$F$_2$H] in CD$_3$CN

| δ, ppm | Multiplicity | J/Hz | Assignment | Integral |
|---|---|---|---|---|
| −81.3 | m | — | trans-CF$_3$ | 3 |
| −82.5 | m | — | cis-CF$_3$ | 6 |
| −114.3 | d, d, m | $^1J_{(PF)}$ = 734<br>$^2J_{(HF)}$ = 63 | [P(C$_2$F$_5$)$_3$F$_2$H]$^-$ | 2 |
| −119.8 | d, m | $^2J_{(PFtrans)}$ = 105 | trans-CF$_2$ | 2 |
| −126.5 | d, m | $^2J_{(PFcis)}$ = 93 | cis-CF$_2$ | 4 |

TABLE 11.3

$^1$H-NMR data of [((CH$_3$)$_2$CH)$_2$N(H)CH$_3$][P(C$_2$F$_5$)$_3$F$_2$H] in CD$_3$CN

| δ, ppm | Multiplicity | J/Hz | Assignment | Integral |
|---|---|---|---|---|
| 1.5 | d | $^3J_{(HH)}$ = 7 | —CH(CH$_3$)$_2$ | 1 |
| 2.8 | s |  | —NCH$_3$ | 0.2 |
| 3.7 | sept | $^3J_{(HH)}$ = 7 | —CH(CH$_3$)$_2$ | 0.15 |
| 5.7 | d, t, quin, m | $^1J_{(PH)}$ = 680 | [P(C$_2$F$_5$)$_3$F$_2$H] | 0.15 |
|  |  | $^2J_{(HF)}$ = 64 |  |  |
|  |  | $^3J_{(HFcis)}$ = 13 |  |  |

TABLE 11.4

$^{13}$C{$^1$H}-NMR data of [((CH$_3$)$_2$CH)$_2$N(H)CH$_3$][P(C$_2$F$_5$)$_3$F$_2$H] in CD$_3$CN

| δ, ppm | Multiplicity | J/Hz | Assignment |
|---|---|---|---|
| 19.3 | s | — | CH$_3$ |
| 32.3 | s | — | NCH$_3$ |
| 56.8 | s | — | NCH |

Example 12

Reaction of [Me$_2$NCH$_2$NMe$_3$][P(C$_2$F$_5$)$_3$F$_2$H] with (PhO)$_2$P(O)H

[(CH$_3$)$_2$NCH$_2$N(CH$_3$)$_3$][(C$_2$F$_5$)$_3$PF$_2$H]+(C$_6$H$_5$O)$_2$P(O)H→(CH$_3$)$_2$NCH$_2$P(O)(OC$_6$H$_5$)$_2$+[HN(CH$_3$)$_3$][(C$_2$F$_5$)$_3$PF$_2$H]

[Me$_2$NCH$_2$NMe$_3$][P(C$_2$F$_5$)$_3$F$_2$H] is dissolved in CH$_2$Cl$_2$, and an excess of (PhO)$_2$PHO is added. The solution is investigated by NMR spectroscopy.

TABLE 12.1

$^{31}$P-NMR data of the products in CH$_2$Cl$_2$

| δ, ppm | Multiplicity | J/Hz | Assignment |
|---|---|---|---|
| 7.3 | t | $^2J_{(PCH2)}$ = 13 | Me$_2$NCH$_2$P(O)(OPh)$_2$ |
| −153.8 | d, t, quin, t | $^1J_{(PH)}$ = 678 | [P(C$_2$F$_5$)$_3$F$_2$H]$^−$ |
|  |  | $^1J_{(PF)}$ = 731 |  |
|  |  | $^2J_{(PFtrans)}$ = 104 |  |
|  |  | $^2J_{(PFcis)}$ = 93 |  |

TABLE 12.2

$^{13}$C{$^1$H}-NMR data of the products in CH$_2$Cl$_2$

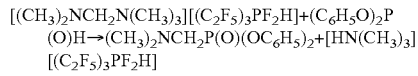

| δ, ppm | Multiplicity | J/Hz | Assignment |
|---|---|---|---|
| 44.7 | s | — | HN(CH$_3$)$_3$$^+$ |
| 45.1 | d | $^3J_{(PC)}$ = 5 | (CH$_3$)$_2$NCH$_2$P(O)(OPh)$_2$ |
| 51.4 | d | $^1J_{(PC)}$ = 157 | (CH$_3$)$_2$NCH$_2$P(O)(OPh)$_2$ |

Example 13

Reaction of [Me$_2$NCH$_2$NMe$_3$][P(C$_2$F$_5$)$_3$F$_2$H] with P(CH$_3$)$_3$

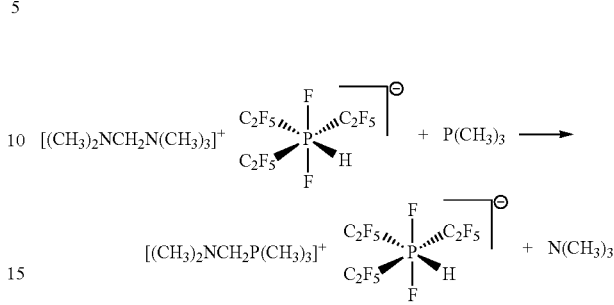

[Me$_2$NCH$_2$NMe$_3$][P(C$_2$F$_5$)$_3$F$_2$H] is dissolved in CH$_2$Cl$_2$, and excess P(CH$_3$)$_3$ is condensed on. The solution is investigated by NMR spectroscopy.

TABLE 13.1

$^{31}$P-NMR data of [(CH$_3$)$_2$NCH$_2$P(CH$_3$)$_3$][P(C$_2$F$_5$)$_3$F$_2$H] in CH$_2$Cl$_2$

| δ, ppm | Multiplicity | J/Hz | Assignment |
|---|---|---|---|
| 24.3 | dec, t | $^2J_{(PCH3)}$ = 13 | [(CH$_3$)$_2$NCH$_2$P(CH$_3$)$_3$]$^+$ |
|  |  | $^2J_{(PCH2)}$ = 4 |  |
|  |  | $^1J_{(PC)}$ = 54 |  |
| −154.1 | d, t, quin, t | $^1J_{(PH)}$ = 678 | [P(C$_2$F$_5$)$_3$F$_2$H]$^−$ |
|  |  | $^1J_{(PF)}$ = 728 |  |
|  |  | $^2J_{(PFtrans)}$ = 105 |  |
|  |  | $^2J_{(PFcis)}$ = 93 |  |

TABLE 13.2

$^{19}$F-NMR data of [(CH$_3$)$_2$NCH$_2$P(CH$_3$)$_3$][P(C$_2$F$_5$)$_3$F$_2$H] in CH$_2$Cl$_2$

| δ, ppm | Multiplicity | J/Hz | Assignment | Integral |
|---|---|---|---|---|
| −80.8 | m | — | trans-CF$_3$ | 3 |
| −82.0 | m | — | cis-CF$_3$ | 6 |
| −113.9 | d, d, m | $^1J_{(PF)}$ = 730 | PF | 2 |
|  |  | $^2J_{(FH)}$ = 63 |  |  |
| −119.2 | d, m | $^2J_{(PFtrans)}$ = 105 | trans-CF$_2$ | 2 |
| −125.7 | d, m | $^2J_{(PFcis)}$ = 93 | cis-CF$_2$ | 4 |

TABLE 13.3

$^1$H-NMR data of [(CH$_3$)$_2$NCH$_2$P(CH$_3$)$_3$][P(C$_2$F$_5$)$_3$F$_2$H] in CH$_2$Cl$_2$

| δ, ppm | Multiplicity | J/Hz | Assignment | Integral |
|---|---|---|---|---|
| 1.8 | d | $^2J_{(PH)}$ = 14 | [(CH$_3$)$_2$NCH$_2$P(CH$_3$)$_3$]$^+$ | 9 |
| 2.4 | s | — | [(CH$_3$)$_2$NCH$_2$P(CH$_3$)$_3$]$^+$ | 6 |
| 3.3 | d | $^2J_{(PH)}$ = 5 | [(CH$_3$)$_2$NCH$_2$P(CH$_3$)$_3$]$^+$ | 2 |

TABLE 13.4

$^{13}$C{$^1$H}-NMR data of [(CH$_3$)$_2$NCH$_2$P(CH$_3$)$_3$][P(C$_2$F$_5$)$_3$F$_2$H] in CH$_2$Cl$_2$

| δ, ppm | Multiplicity | J/Hz | Assignment |
|---|---|---|---|
| 6.5 | d | $^1J_{(PC)}$ = 54 | [(CH$_3$)$_2$NCH$_2$P(CH$_3$)$_3$]$^+$ |
| 47.6 | d | $^3J_{(PC)}$ = 7 | [(CH$_3$)$_2$NCH$_2$P(CH$_3$)$_3$]$^+$ |
| 51.6 | s (br) | — | N(CH$_3$)$_3$ |
| 52.9 | d | $^1J_{(PC)}$ = 7 | [(CH$_3$)$_2$NCH$_2$P(CH$_3$)$_3$]$^+$ |

The invention claimed is:

1. A process for the preparation of a compound of formula (1)

$$[Kt]^{x+}[(C_nF_{2n+1})_zPF_{5-z}H]^-{}_x, \quad (1)$$

in which $[Kt]^{x+}$ is an inorganic or organic cation, n is 1-8, x is 1-4, and z is 1-4, said process comprising:

in a first step, reacting a compound of formula (2)

$$(C_nF_{2n+1})_zPF_{5-z} \quad (2)$$

with a hydride ion donor, and
if $[Kt]^{x+}$ in formula (1) is an organic cation, in a second step, optionally reacting the product from said first step with a compound of formula (3)

$$[Kt]^{x+}[X]^-{}_x, \quad (3),$$

in which $[Kt]^{x+}$ stands for an organic cation and $[X]^-$ stands for a hydrophilic anion.

2. The process according to claim 1, wherein said hydride ion donor is selected from metal hydrides, borohydrides, hydridoborates, hydridoaluminates and tertiary and secondary amines.

3. The process according to claim 2, wherein said hydride ion donor is $LiAlH_4$.

4. The process according to claim 2, wherein said hydride ion donor is a tertiary or secondary amine of formula (11)

$$R^{14}{}_2N-CH_2R^{15} \quad (11),$$

where $R^{14}$ and $R^{15}$ on each occurrence, independently of one another, denotes H, where a maximum of one substituent $R^{14}$ can be H,
straight-chain or branched alkyl having 1-20 C atoms,
straight-chain or branched alkenyl having 2-20 C atoms and one or more double bonds,
straight-chain or branched alkynyl having 2-20 C atoms and one or more triple bonds,
saturated, partially or fully unsaturated cycloalkyl having 3-7 C atoms, which may be substituted by alkyl groups having 1-6 C atoms,
where $R^{15}$ may also be Cl or F,
where $R^{15}$ may be fully substituted by fluorine and/or one or more $R^{14}$ and/or $R^{15}$ may be partially substituted by halogens or partially substituted by $-OR^{1*}$, $-NR^{1*}{}_2$, $-CN$, $-C(O)NR^{1*}{}_2$ or $-SO_2NR^{1*}{}_2$,
and where one or two non-adjacent carbon atoms which are not in the α-position of the radicals $R^{14}$ and/or $R^{15}$ are each optionally replaced by atoms and/or atom groups selected from $-O-$, $-S-$, $-S(O)-$, $-SO_2-$, $-N^+R^{1*}{}_2-$, $-C(O)NR^{1*}-$, $-SO_2NR^{1*}-$ and $-P(O)R^{1*}-$; and
$R^{1*}$ is a non- or partially fluorinated $C_1$- to $C_6$-alkyl, $C_3$- to $C_7$-cycloalkyl, unsubstituted or substituted phenyl.

5. The process according to claim 1, wherein z stands for 2 or 3.

6. The process according to claim 1, wherein $[Kt]^{x+}$ is a metal cation.

7. The process according to claim 1, wherein $[Kt]^{x+}$ is an organic cation.

8. The process according to claim 7, wherein the cation $[Kt]^{x+}$ is selected from ammonium, phosphonium, uronium, thiouronium, sulfonium, oxonium, guanidinium cations, heterocyclic cations and iminium cations, where ammonium cations are given by formula (4)

$$[NR_4]^+ \quad (4),$$

where

R in each case, independently of one another, denotes

H,
straight-chain or branched alkyl having 1-20 C atoms,
straight-chain or branched alkenyl having 2-20 C atoms and one or more double bonds,
straight-chain or branched alkynyl having 2-20 C atoms and one or more triple bonds,
saturated, partially or fully unsaturated cycloalkyl having 3-7 C atoms, which may be substituted by alkyl groups having 1-6 C atoms,
where one R may be fully substituted by fluorine and/or one or more R may be partially substituted by halogens or partially substituted by $-OR^1$, $-NR^{1*}{}_2$, $-CN$, $-C(O)NR^1{}_2$ or $-SO_2NR^1{}_2$,
and where one or two non-adjacent carbon atoms which are not in the α-position of the radical R are each optionally replaced by atoms and/or atom groups selected $-O-$, S, $S(O)-$, $-SO_2-$, $-N^+R^1{}_2-$, $-C(O)NR^1-$, $-SO_2NR^1-$ and $-P(O)R^1-$;
where phosphonium cations are given by formula (5)

$$[PR^2{}_4]^+ \quad (5),$$

where $R^2$ in each case, independently of one another, denotes
H where all substituents $R^2$ cannot simultaneously be H, $NR^1{}_2$,
straight-chain or branched alkyl having 1-20 C atoms,
straight-chain or branched alkenyl having 2-20 C atoms and one or more double bonds,
straight-chain or branched alkynyl having 2-20 C atoms and one or more triple bonds,
saturated, partially or fully unsaturated cycloalkyl having 3-7 C atoms, which may be substituted by alkyl groups having 1-6 C atoms,
where one $R^2$ may be fully substituted by fluorine and/or one or more $R^2$ may be partially substituted by halogens, or partially substituted by $-OR^1$, $-CN$, $-C(O)NR^1{}_2$, or $-SO_2NR^1{}_2$,
and where one or two non-adjacent carbon atoms which are not in the α-position of the $R^2$ are each optionally replaced by atoms and/or atom groups selected from $-O-$, $-S-$, $-S(O)-$, $-SO_2-$, $-N^+R^1{}_2-$, $-C(O)NR^1-$, $-SO_2NR^1-$, and $-P(O)R^1-$;
where uronium cations are given by formula (6)

$$[C(NR^3R^4)(OR^5)(NR^6R^7)]^+ \quad (6)$$

and thiouronium cations are given by formula (7)

$$[C(NR^3R^4)(SR^5)(NR^6R^7)]^+ \quad (7),$$

where $R^3$ to $R^7$ each, independently of one another, denote
H, $NR^{1*}{}_2$,
straight-chain or branched alkyl having 1 to 20 C atoms,
straight-chain or branched alkenyl having 2-20 C atoms and one or more double bonds,
straight-chain or branched alkynyl having 2-20 C atoms and one or more triple bonds,
saturated, partially or fully unsaturated cycloalkyl having 3-7 C atoms,
which may be substituted by alkyl groups having 1-6 C atoms,
where one or more of the substituents $R^3$ to $R^7$ may be partially substituted by halogens, or by $-OH$, $-OR^1$, $-CN$, $-C(O)NR^1{}_2$, or $-SO_2NR^1{}_2$,
and where one or two non-adjacent carbon atoms which are not in the α-position of $R^3$ to $R^7$ are each optionally replaced by atoms and/or atom groups selected from —O—, —S—, —S(O)—, —SO$_2$—, —N$^+$R$^1_2$—, —C(O)NR$^1$—, —SO$_2$NR$^1$—, and —P(O)R$^1$—;
where sulfonium cations are given by formula (12))

[(R$^o_3$S)]$^+$ (12), where
R$^o$ stands for
NR'''$_2$,
straight-chain or branched alkyl having 1-8 C atoms,
saturated, partially or fully unsaturated cycloalkyl having 3-7 C atoms, which may be substituted by alkyl groups having 1-6 C atoms,
where one or more of the substituents R$^o$ may be partially substituted by halogens, or by —OR''', —CN or —N(R''')$_2$;
where oxonium cations are given by formula (13)

[(R$^{o*}$)$_3$O]$^+$ (13), where
R$^{o*}$ stands for
straight-chain or branched alkyl having 1-8 C atoms,
saturated, partially or fully unsaturated cycloalkyl having 3-7 C atoms, which may be substituted by alkyl groups having 1-6 C atoms,
where one or more of the substituents R$^{o*}$ may be partially substituted by halogens, or by —OR''', —CN or —N(R''')$_2$;
where guanidinium cations are given by formula (8)

[C(NR$^8$R$^9$)(NR$^{10}$R$^{11}$)(NR$^{12}$R$^{13}$)]+ (8), where
R$^8$ to R$^{13}$ each, independently of one another, denote H, NR$^{1*}_2$,
straight-chain or branched alkyl having 1 to 20 C atoms,
straight-chain or branched alkenyl having 2-20 C atoms and one or more double bonds,
straight-chain or branched alkynyl having 2-20 C atoms and one or more triple bonds,
saturated, partially or fully unsaturated cycloalkyl having 3-7 C atoms, which may be substituted by alkyl groups having 1-6 C atoms,
where one or more of the substituents R$^8$ to R$^{13}$ may be partially substituted by halogens or by —OR$^1$, —CN, —C(O)NR$^1_2$, or —SO$_2$NR$^1_2$,
and where one or two non-adjacent carbon atoms which are not in the α-position of R$^8$ to R$^{13}$ are each optionally replaced by atoms and/or atom groups selected from —O—, —S—, —S(O)—, —SO$_2$—, —N$^+$R$^1_2$—, —C(O)NR$^1$—, —SO$_2$NR$^1$—, and —P(O)R$^1$—;
where heterocyclic cations are given by formula (9)

[HetN]$^+$ (9), where [HetN]$^+$ is a heterocyclic cation selected from

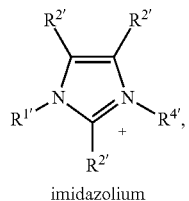
imidazolium

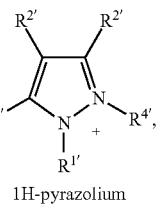
1H-pyrazolium

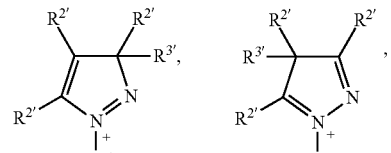
3H-pyrazolium  4H-pyrazolium

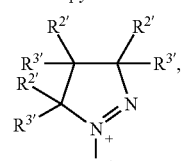
1-pyrazolinium

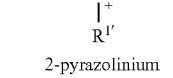
2-pyrazolinium

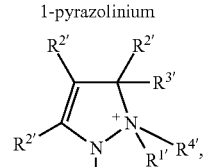
3-pyrazolinium

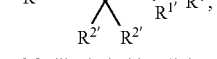
2,3-dihydroimidazolinium

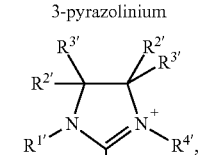
4,5-dihydroimidazolinium

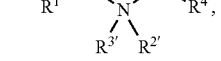
2,5-dihydroimidazolinium

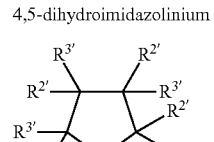
pyrrolidinium

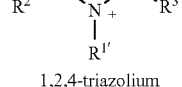
1,2,4-triazolium

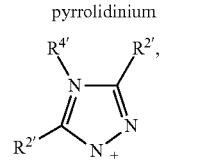
1,2,4-triazolium

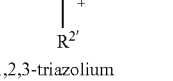
1,2,3-triazolium

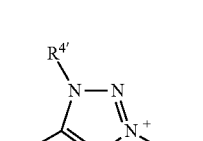
1,2,3-triazolium

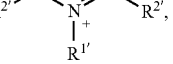
pyridinium

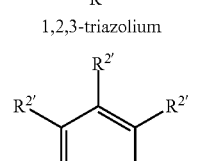
pyridazinium

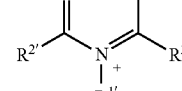
pyrimidinium

-continued

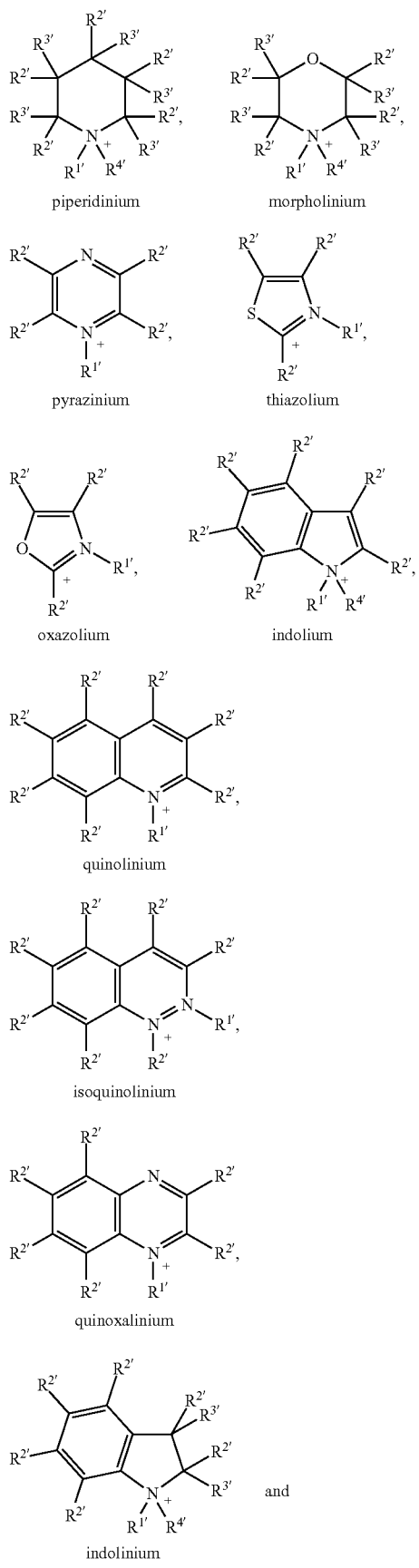

piperidinium morpholinium pyrazinium thiazolium oxazolium indolium quinolinium isoquinolinium quinoxalinium indolinium and

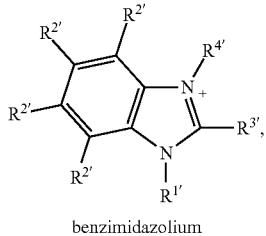

benzimidazolium where the substituents $R^{1'}$ to $R^{4'}$ each, independently of one another, denote
H,
straight-chain or branched alkyl having 1-20 C atoms,
straight-chain or branched alkenyl having 2-20 C atoms and one or more double bonds,
straight-chain or branched alkynyl having 2-20 C atoms and one or more triple bonds,
saturated, partially or fully unsaturated cycloalkyl having 3-7 C atoms, which may be substituted by alkyl groups having 1-6 C atoms,
saturated, partially or fully unsaturated heteroaryl, heteroaryl-$C_1$-$C_6$-alkyl or aryl-$C_1$-$C_6$-alkyl,
where the substituents $R^{1'}$, $R^{2'}$, $R^{3'}$ and/or $R^{4'}$ together may form a ring system, where one or more substituents $R^{1'}$ to $R^{4'}$ may be partially or fully substituted by halogens or partially substituted by —$OR^1$, —CN, —C(O)$NR^1_2$, or —$SO_2NR^1_2$, but where $R^{1'}$ and $R^{4'}$ cannot simultaneously be fully substituted by halogens, and where one or two non-adjacent carbon atoms which are not bonded to the heteroatom of the substituents $R^{1'}$ to $R^{4'}$ are each optionally replaced by atoms and/or atom groups selected from —O—, —S—, —S(O)—, —$SO_2$—, —$N^+R^1_2$—, —C(O)$NR^1$—, —$SO_2NR^1$—, and —P(O)$R^1$—; and
where iminium cations are given by formula (10)

$$[R^{14}_2N=CHR^{15}]^+ \quad (10),$$

where
$R^{14}$ and $R^{15}$ on each occurrence, independently of one another, denotes
H, where a maximum of one substituent $R^{14}$ can be H,
straight-chain or branched alkyl having 1-20 C atoms,
straight-chain or branched alkenyl having 2-20 C atoms and one or more double bonds,
straight-chain or branched alkynyl having 2-20 C atoms and one or more triple bonds,
saturated, partially or fully unsaturated cycloalkyl having 3-7 C atoms, which may be substituted by alkyl groups having 1-6 C atoms,
where $R^{15}$ may also stand for Cl or F,
where $R^{15}$ may be fully substituted by fluorine and/or one or more $R^{14}$ and/or $R^{15}$ may be partially substituted by halogens or partially substituted by —$OR^{1*}$, —$NR^{1*}_2$, —CN, —C(O)$NR^{1*}_2$ or —$SO_2NR^{1*}_2$,
and where one or two non-adjacent carbon atoms which are not in the α-position of the radical $R^{14}$ and/or $R^{15}$ are each optionally replaced by atoms and/or atom groups selected from —O—, —S—, —S(O)—, —$N^+R^{1*}_2$—, —C(O)$NR^{1*}$—, —$SO_2NR^{1*}$— and —P(O)$R^{1*}$—;
in which
$R^1$ stands for H, non- or partially fluorinated $C_1$- to $C_6$-alkyl, $C_3$- to $C_7$-cycloalkyl, unsubstituted or substituted phenyl, R¹* stands for non- or partially fluorinated $C_1$- to $C_6$-alkyl, $C_3$- to $C_7$-cycloalkyl, unsubstituted or substituted phenyl, and R''' stands for a straight-chain or branched $C_1$-$C_8$-alkyl.

9. The process according to claim 1, wherein the reaction in the first step is carried out at −80 to 50° C.

10. A process comprising reacting a compound of formula (1)

$$[Kt]^{x+}[(c_nF_{2n+1})_zPF_{5-z}H]^-{}_x \qquad (1)$$

in which $[Kt]^{x+}$ is an inorganic cation, n is 1-8, x is 1-4, and z is 1-4, with a compound of formula (3)

$$[Kt]^{x+}[X]^-{}_x \qquad (3),$$

in which $[Kt]^{x+}$ is an organic cation and $[X]^-$ stands for a hydrophilic anion.

11. An electrolyte composition comprising a compound of formula (1)

$$[Kt]^{x+}[(C_nF_{2n+1})_zPF_{5-z}H]^-{}_x \qquad (1)$$

in which $[Kt]^{x+}$ is an organic cation, n is 1-8, x is 1-4, and z is 1-4.

12. A compound of formula (1)

$$[Kt]^{x+}[(C_nF_{2n+1})_zPF_{5-z}H]^-{}_x \qquad (1)$$

in which $[Kt]^{x+}$ is an inorganic or organic cation, n is 1-8, x is 1-4, and z is 1-4, where the compounds $[(CF_3)_2PF_3H]^-K^+$, $[(CF_3)_2PF_3H]^-[(CH_3)_2NH_2]^+$, $[(CF_3)PF_4H]^-K^+$ and $[(CF_3)PF_4H]^-[(CH_3)_2NH_2]^+$ are excluded.

13. A compound according to claim 12, wherein $[Kt]^{x+}$ is a metal cation.

14. A compound according to claim 12, wherein $[Kt]^{x+}$ is an organic cation.

15. A process comprising:

converting a compound according to claim 1, in which $[Kt]^{x+}$ stands for an organic cation, into a compound containing a $[(C_nF_{2n+1})_2P(O)O]^-$ or $[(C_nF_{2n+1})P(O)O_2]^{-2}$ anion by hydrolysis.

16. The process according to claim 1, wherein the product from said first step is reacted with a compound of formula (3) to obtain a compound of formula (1) in which $[Kt]^{x+}$ stands for an organic cation.

17. The process according to claim 1, wherein said hydride ion donor is a metal hydride and the product from said first step is reacted with a compound of formula (3) to obtain a compound of formula (1) in which $[Kt]^{x+}$ stands for an organic cation.

18. The process according to claim 1, wherein n stands for 2, 3 or 4.

19. The process according to claim 5, wherein n stands for 2, 3 or 4.

20. The process according to claim 1, wherein compound of formula (2) is $(C_2F_5)_3PF_2$.

21. The process according to claim 1, wherein $[Kt]^{x+}$ is an inorganic cation which is a metal cation selected from lithium, sodium, and potassium cations.

22. The process according to claim 1, wherein $[Kt]^{x+}$ is an organic cation selected from propyl(dimethyl)ethylammonium, methoxyethyl(dimethyl)ethylammonium, 1-butyl-1-methylpyrrolidinium, 1-propyl-1-methylpyrrolidinium, 1-methoxyethyl-1-methylpyrrolidinium, 1-ethyl-3-methylimidazolium, 1-butyl-3-methylimidazolium and 1-methyl-3-propylimidazolium.

23. The process according to claim 1, wherein $[Kt]^{x+}$ is an organic cation selected from 1-ethyl-3-methylimidazolium and 1-butyl-3-methylimidazolium.

24. The process according to claim 16, wherein $[X]^-$ is an anion selected from $Cl^-$, $Br^-$, $I^-$, sulfate, sulfonate, acetate and $BF_4^-$.

25. The process according to claim 1, wherein the reaction in the first step is carried out at a temperature of −80 to 50° C. in the presence of an aprotic solvent.

26. The process according to claim 25, wherein said aprotic solvent is dioxane, tetrahydrofuran, diethyl ether, methyl tert-butyl ether, hexane, cyclohexane, benzene, dichloromethane or dichloroethane.

27. The process according to claim 16, wherein the reaction in the second step is carried out at room temperature in the presence of water or in a mixture of water and organic solvent.

\* \* \* \* \*

UNITED STATES PATENT AND TRADEMARK OFFICE
CERTIFICATE OF CORRECTION

PATENT NO. : 8,916,729 B2
APPLICATION NO. : 13/516029
DATED : December 23, 2014
INVENTOR(S) : Nikolai Mykola Ignatyev et al.

It is certified that error appears in the above-identified patent and that said Letters Patent is hereby corrected as shown below:

In the Claims

Column 38, Line 25, second structure reads:

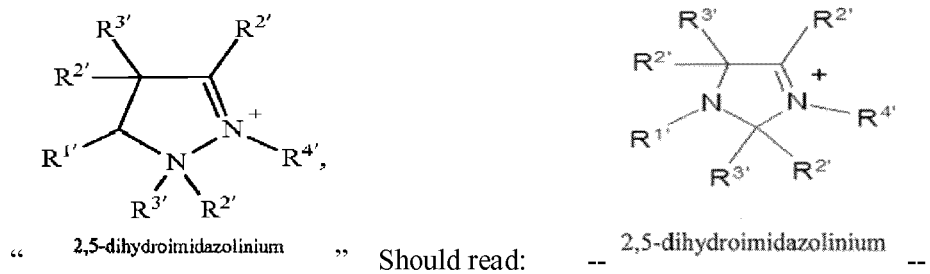

Column 38, Line 40 reads:

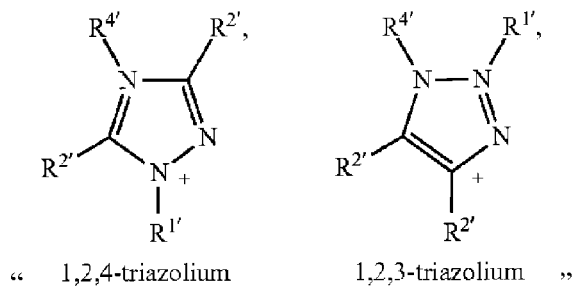

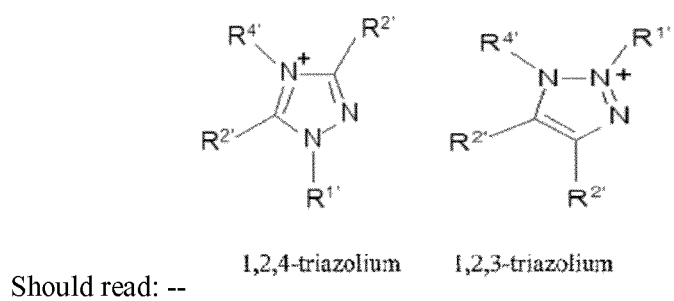

Should read: --

Signed and Sealed this
Twelfth Day of January, 2016

Michelle K. Lee
*Director of the United States Patent and Trademark Office*

CERTIFICATE OF CORRECTION (continued)
U.S. Pat. No. 8,916,729 B2

Column 39, Line 40 reads:

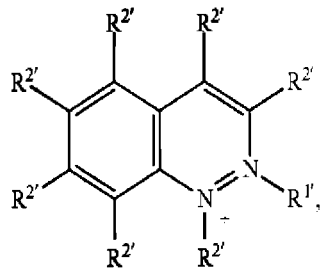

" isoquinolinium " Should read: --

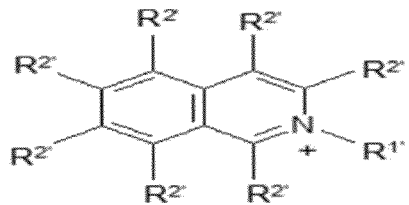

isoquinolinium, --

Column 40, Line 62 reads:

selected from —O—, —S—, —S(O)—, —N$^+$R$^{1*}_2$—,

Should read:

-- selected from -O-, -S-, -S(O)-, -SO$_2$-, -N$^+$R$^{1*}_2$-, --